(12) United States Patent
Triplett et al.

(10) Patent No.: US 10,702,290 B2
(45) Date of Patent: Jul. 7, 2020

(54) ORTHOPEDIC FASTENER, RETAINER, AND GUIDE

(71) Applicant: First Ray, LLC, Logan, UT (US)

(72) Inventors: Daniel J. Triplett, Providence, UT (US); T. Wade Fallin, Hyde Park, UT (US)

(73) Assignee: First Ray, LLC, Logan, UT (US)

( * ) Notice: Subject to any disclaimer, the term of this patent is extended or adjusted under 35 U.S.C. 154(b) by 370 days.

(21) Appl. No.: 15/295,496

(22) Filed: Oct. 17, 2016

(65) Prior Publication Data

US 2017/0119405 A1 May 4, 2017

Related U.S. Application Data

(60) Provisional application No. 62/249,687, filed on Nov. 2, 2015.

(51) Int. Cl.
*A61B 17/17* (2006.01)
*A61B 17/56* (2006.01)
(Continued)

(52) U.S. Cl.
CPC .............. *A61B 17/17* (2013.01); *A61B 17/16* (2013.01); *A61B 17/1728* (2013.01); *A61B 17/683* (2013.01); *A61B 17/86* (2013.01); *A61B 17/8665* (2013.01); *A61B 17/8866* (2013.01); *A61B 17/8872* (2013.01);
(Continued)

(58) Field of Classification Search
CPC ..... A61B 17/17; A61B 17/16; A61B 17/1728; A61B 17/683; A61B 17/86; A61B 17/8665; A61B 17/8866; A61B 17/8872; A61B 17/8057; A61B 17/885; A61B 17/861; A61B 17/82; A61B 17/844; A61B 17/6441; A61B 17/6425; A61B 17/1615; A61B 17/1714; A61B 17/1775; A61B 2017/867; A61B 2017/00407; A61B 2017/681;
(Continued)

(56) References Cited

U.S. PATENT DOCUMENTS 2,133,859 A 10/1938 Hawley
2,485,531 A 10/1949 Dzus
(Continued)

FOREIGN PATENT DOCUMENTS

DE 1935101 A1 1/1971
EP 1679044 A2 7/2006
(Continued)

OTHER PUBLICATIONS

US 9,125,700 B2, 09/2015, Gonzalez-Hernandez (withdrawn)
(Continued)

*Primary Examiner* — Jessica Weiss
(74) *Attorney, Agent, or Firm* — David Meibos; Maywood IP Law

(57) ABSTRACT

Implants, instruments, and methods for connecting and/or stabilizing first and second bone portions relative to one another are presented including fasteners and retainers connectable in axial force transmitting relationship and instruments for their installation. In one example a guide is configured to clamp two bone portions together while a fastener is inserted through at least one of the bone portions to engage a retainer.

18 Claims, 18 Drawing Sheets

(51) Int. Cl.
  *A61B 17/68* (2006.01)
  *A61B 17/86* (2006.01)
  *A61B 17/88* (2006.01)
  *A61B 17/16* (2006.01)
  *A61B 17/80* (2006.01)
  *A61B 90/00* (2016.01)
  *A61B 17/00* (2006.01)

(52) U.S. Cl.
  CPC . *A61B 17/8057* (2013.01); *A61B 2017/00407* (2013.01); *A61B 2017/867* (2013.01); *A61B 2090/062* (2016.02)

(58) Field of Classification Search
  CPC ..... A61B 2017/8655; A61B 2017/0403–0406; A61B 2017/0409; A61B 2017/0411
  USPC ....... 606/300–321, 96–98, 104, 86 R, 87–89
  See application file for complete search history.

(56) References Cited

U.S. PATENT DOCUMENTS

| | | | | |
|---|---|---|---|---|
| 2,489,870 | A | 11/1949 | Dzus | |
| 2,511,051 | A * | 6/1950 | Dzus | A61B 17/683 81/451 |
| 2,760,488 | A | 8/1956 | Pierce | |
| 2,825,329 | A | 3/1958 | Caesar | |
| 3,618,447 | A | 11/1971 | Goins | |
| 3,709,218 | A | 1/1973 | Halloran | |
| 3,939,828 | A | 2/1976 | Mohr | |
| 4,047,524 | A | 9/1977 | Hall | |
| 4,060,089 | A | 11/1977 | Noiles | |
| 4,456,005 | A | 6/1984 | Lichty | |
| 4,635,637 | A | 1/1987 | Schreiber | |
| 4,688,561 | A | 8/1987 | Reese | |
| 4,696,300 | A | 9/1987 | Anderson | |
| 4,736,746 | A | 4/1988 | Anderson | |
| 4,838,254 | A | 6/1989 | Gauthier | |
| 4,841,960 | A | 6/1989 | Garner | |
| 4,994,073 | A | 2/1991 | Green | |
| 5,053,038 | A | 10/1991 | Sheehan | |
| 5,085,661 | A | 2/1992 | Moss | |
| 5,152,764 | A * | 10/1992 | Goble | A61B 17/1714 606/96 |
| 5,250,049 | A | 10/1993 | Michael | |
| 5,269,783 | A | 12/1993 | Sander | |
| 5,293,881 | A | 3/1994 | Green | |
| 5,312,412 | A | 5/1994 | Whipple | |
| 5,314,429 | A | 5/1994 | Goble | |
| 5,330,468 | A | 7/1994 | Burkhart | |
| 5,336,240 | A | 8/1994 | Metzler | |
| 5,341,622 | A | 8/1994 | Odermatt | |
| 5,344,005 | A | 9/1994 | Kettner | |
| 5,350,060 | A | 9/1994 | Alpern | |
| 5,350,380 | A | 9/1994 | Goble | |
| 5,354,300 | A | 10/1994 | Goble | |
| 5,358,624 | A | 10/1994 | Roshdy | |
| 5,374,268 | A | 12/1994 | Sander | |
| 5,383,367 | A | 1/1995 | Goble | |
| 5,514,144 | A * | 5/1996 | Bolton | A61B 17/1714 606/96 |
| 5,601,571 | A | 2/1997 | Moss | |
| 5,643,319 | A | 7/1997 | Green | |
| 5,658,313 | A | 8/1997 | Thal | |
| 5,665,112 | A | 9/1997 | Thal | |
| 5,674,247 | A | 10/1997 | Sohn | |
| 5,697,933 | A * | 12/1997 | Gundlapalli | A61B 17/1714 606/206 |
| 5,725,532 | A * | 3/1998 | Shoemaker | A61B 17/1775 623/1.11 |
| 5,728,136 | A | 3/1998 | Thal | |
| 5,810,822 | A | 9/1998 | Mortier | |
| 5,873,891 | A | 2/1999 | Sohn | |
| 5,891,168 | A | 4/1999 | Thal | |
| 5,919,194 | A | 7/1999 | Anderson | |
| 5,921,986 | A | 7/1999 | Bonutti | |
| 5,954,747 | A | 9/1999 | Clark | |
| 6,001,101 | A | 12/1999 | Augagneur | |
| 6,027,504 | A * | 2/2000 | McGuire | A61B 17/0206 128/898 |
| 6,030,162 | A | 2/2000 | Huebner | |
| 6,117,160 | A | 9/2000 | Bonutti | |
| 6,149,669 | A | 11/2000 | Li | |
| 6,179,839 | B1 | 1/2001 | Weiss | |
| 6,190,401 | B1 | 2/2001 | Green | |
| 6,203,545 | B1 | 3/2001 | Stofella | |
| 6,210,415 | B1 | 4/2001 | Bester | |
| 6,248,109 | B1 | 6/2001 | Stofella | |
| 6,258,091 | B1 | 7/2001 | Sevrain | |
| 6,277,130 | B1 | 8/2001 | Shadduck | |
| 6,302,887 | B1 | 10/2001 | Spranza | |
| 6,306,159 | B1 | 10/2001 | Schwartz | |
| 6,364,884 | B1 | 4/2002 | Bowman | |
| 6,402,766 | B2 | 6/2002 | Bowman | |
| 6,423,073 | B2 | 7/2002 | Bowman | |
| 6,436,110 | B2 | 8/2002 | Bowman | |
| 6,447,517 | B1 | 9/2002 | Bowman | |
| 6,497,707 | B1 | 12/2002 | Bowman | |
| 6,533,802 | B2 | 3/2003 | Bojarksi | |
| 6,554,852 | B1 | 4/2003 | Oberlander | |
| 6,589,244 | B1 | 7/2003 | Sevrain | |
| 6,635,073 | B2 | 10/2003 | Bonutti | |
| 6,669,698 | B1 | 12/2003 | Tromanhauser | |
| 6,743,233 | B1 | 6/2004 | Baldwin | |
| 6,689,136 | B2 | 11/2004 | Stoffella | |
| 6,818,010 | B2 | 11/2004 | Eichhorn | |
| 6,918,912 | B2 * | 7/2005 | Seemann | A61B 17/683 606/308 |
| 6,921,401 | B2 | 7/2005 | Lerch | |
| 6,942,668 | B2 | 9/2005 | Padget | |
| 6,972,027 | B2 | 12/2005 | Fallin | |
| 7,008,428 | B2 | 3/2006 | Cachia | |
| 7,060,068 | B2 | 6/2006 | Tromanhauser | |
| 7,087,073 | B2 | 8/2006 | Bonutti | |
| 7,153,309 | B2 | 12/2006 | Huebner | |
| 7,214,232 | B2 | 5/2007 | Bowman | |
| 7,326,213 | B2 | 2/2008 | Benderev | |
| 7,344,538 | B2 | 3/2008 | Myerson | |
| 7,468,074 | B2 | 12/2008 | Caborn | |
| 7,491,220 | B2 | 2/2009 | Coughln | |
| 7,563,275 | B2 | 7/2009 | Falahee | |
| 7,578,825 | B2 | 8/2009 | Huebner | |
| 7,582,107 | B2 | 9/2009 | Trail | |
| 7,588,594 | B2 | 9/2009 | Sander | |
| 7,603,192 | B2 | 10/2009 | Martin | |
| 7,608,094 | B2 | 10/2009 | Falahee | |
| 7,625,395 | B2 | 12/2009 | Muckter | |
| 7,708,738 | B2 | 5/2010 | Fourcault | |
| 7,771,457 | B2 | 8/2010 | Kay | |
| 7,785,355 | B2 | 8/2010 | Mohr | |
| 7,837,717 | B2 | 11/2010 | Deffenbaugh | |
| 7,875,063 | B1 | 1/2011 | Sander | |
| 7,922,750 | B2 * | 4/2011 | Trautwein | A61B 17/1606 606/279 |
| 7,931,680 | B2 | 4/2011 | Myerson | |
| 7,950,559 | B2 | 5/2011 | Peterson | |
| 7,951,198 | B2 | 5/2011 | Sucec | |
| 8,002,812 | B2 | 8/2011 | Falahee | |
| 8,012,080 | B2 | 9/2011 | Chu | |
| 8,016,867 | B2 | 9/2011 | Bowman | |
| 8,034,076 | B2 | 10/2011 | Criscuolo | |
| 8,062,297 | B2 | 11/2011 | Faillace | |
| 8,062,301 | B2 | 11/2011 | Ammann | |
| 8,097,007 | B2 | 1/2012 | Evans | |
| 8,100,939 | B2 | 1/2012 | Peterson | |
| 8,100,954 | B2 | 1/2012 | Kay | |
| 8,114,101 | B2 | 2/2012 | Criscuolo | |
| 8,118,836 | B2 | 2/2012 | Denham | |
| 8,118,848 | B2 | 2/2012 | Ducharme | |
| 8,133,283 | B2 | 3/2012 | Wilson | |
| 8,137,382 | B2 | 3/2012 | Denham | |
| 8,162,996 | B2 | 4/2012 | Schelling | |
| 8,167,918 | B2 | 5/2012 | Strnad | |
| 8,187,308 | B2 | 5/2012 | Mullaney | |

(56) References Cited

U.S. PATENT DOCUMENTS

| | | | |
|---|---|---|---|
| 8,206,400 B2 | 6/2012 | Falahee | |
| 8,231,627 B2 | 7/2012 | Huebner | |
| 8,235,995 B2 | 8/2012 | Focht | |
| 8,257,403 B2 | 9/2012 | Den Hartog | |
| 8,257,406 B2 | 9/2012 | Kay | |
| 8,262,706 B2 | 9/2012 | Olms | |
| 8,292,898 B2 | 10/2012 | Castaneda | |
| 8,313,492 B2 | 11/2012 | Wong | |
| 8,313,517 B2 | 11/2012 | Mohr | |
| 8,337,537 B2 | 12/2012 | Pelo | |
| 8,348,980 B2 | 1/2013 | Prasad | |
| 8,357,186 B2 | 1/2013 | Hadi | |
| 8,361,113 B2 | 1/2013 | Stone | |
| 8,382,807 B2 | 2/2013 | Austin | |
| 8,419,745 B2 | 4/2013 | Sixto | |
| 8,425,574 B2 | 4/2013 | Huebner | |
| 8,449,561 B2 | 5/2013 | Bowman | |
| 8,518,088 B2 | 8/2013 | Castaneda | |
| 8,535,355 B2 | 9/2013 | Prasad | |
| 8,551,107 B2 | 10/2013 | Ng | |
| 8,574,266 B2 | 11/2013 | Falahee | |
| 8,585,742 B2 | 11/2013 | Windolf | |
| 8,585,744 B2 | 11/2013 | Duggal | |
| 8,591,545 B2 | 11/2013 | Lunn | |
| 8,597,300 B2 | 12/2013 | Deffenbaugh | |
| 8,597,311 B2 | 12/2013 | Criscuolo | |
| 8,617,227 B2 | 12/2013 | Sucec | |
| 8,652,136 B2 | 2/2014 | Yang | |
| 8,652,171 B2 | 2/2014 | Stone | |
| 8,657,820 B2 | 2/2014 | Kubiak | |
| 8,668,718 B2 | 3/2014 | Euteneuer | |
| 8,679,123 B2 | 3/2014 | Kinmon | |
| 8,728,102 B2 | 5/2014 | Criscuolo | |
| 8,734,492 B2 | 5/2014 | Mohr | |
| 8,747,408 B2 | 6/2014 | Falahee | |
| 8,758,414 B2 | 6/2014 | Ng | |
| 8,763,878 B2 | 7/2014 | Euteneuer | |
| 8,764,763 B2 | 7/2014 | Wong | |
| 8,778,000 B2 | 7/2014 | Haddad | |
| 8,789,736 B2 | 7/2014 | Dudai | |
| 8,790,368 B2 | 7/2014 | Sullivan | |
| 8,808,336 B2 | 8/2014 | Duggal | |
| 8,821,536 B2 | 9/2014 | Euteneuer | |
| 8,821,537 B2 | 9/2014 | Euteneuer | |
| 8,834,534 B2 | 9/2014 | Impellizzeri | |
| 8,840,642 B2 | 9/2014 | Euteneuer | |
| 8,845,725 B2 | 9/2014 | Barwood | |
| 8,920,464 B2 | 12/2014 | Euteneuer | |
| 8,926,495 B2 | 1/2015 | Chu | |
| 8,940,016 B2 | 1/2015 | Peterson | |
| 8,951,287 B1 | 2/2015 | Green | |
| 8,998,969 B2 | 4/2015 | Deffenbaugh | |
| 9,011,501 B2 | 4/2015 | Mikhail | |
| 9,027,819 B2 | 5/2015 | Euteneuer | |
| 9,033,201 B2 | 5/2015 | Euteneuer | |
| 9,095,337 B2 | 8/2015 | Euteneuer | |
| 9,095,338 B2 | 8/2015 | Taylor | |
| 9,107,745 B2 | 8/2015 | Bouduban | |
| 9,247,963 B2 * | 2/2016 | Kollmer | A61B 17/683 606/308 |
| 9,433,452 B2 | 9/2016 | Weiner | |
| 9,463,012 B2 | 10/2016 | Bonutti | |
| 10,357,260 B2 * | 7/2019 | Triplett | A61B 17/8665 606/96 |
| 2002/0019649 A1 | 2/2002 | Sikora | |
| 2002/0052628 A1 | 5/2002 | Bowman | |
| 2002/0095157 A1 | 7/2002 | Bowman | |
| 2002/0169452 A1 | 11/2002 | Tormala | |
| 2003/0032961 A1 | 2/2003 | Pelo | |
| 2003/0040746 A1 * | 2/2003 | Mitchell | A61B 17/1606 623/17.11 |
| 2003/0045881 A1 | 3/2003 | Barouk | |
| 2003/0105464 A1 | 6/2003 | Schreurs | |
| 2003/0125743 A1 | 7/2003 | Roman | |
| 2003/0143918 A1 | 8/2003 | Putnam | |
| 2003/0153918 A1 | 8/2003 | Putnam et al. | |
| 2003/0167072 A1 | 9/2003 | Oberlander | |
| 2003/0171754 A1 | 9/2003 | Del Medico | |
| 2004/0015171 A1 | 1/2004 | Bojarski | |
| 2004/0092937 A1 | 5/2004 | Criscuolo | |
| 2004/0127908 A1 | 7/2004 | Roman | |
| 2004/0138664 A1 | 7/2004 | Bowman | |
| 2004/0138683 A1 | 7/2004 | Shelton | |
| 2004/0138705 A1 | 7/2004 | Heino | |
| 2004/0162561 A1 * | 8/2004 | Marchyn | A61B 17/1677 606/78 |
| 2004/0210234 A1 | 10/2004 | Coillard | |
| 2005/0033302 A1 | 2/2005 | Frank | |
| 2005/0085819 A1 | 4/2005 | Ellis | |
| 2005/0143734 A1 | 6/2005 | Cachia | |
| 2005/0149033 A1 * | 7/2005 | McGuire | A61F 2/0811 606/77 |
| 2005/0159762 A1 | 7/2005 | Nuutinen | |
| 2006/0015102 A1 | 1/2006 | Toullec | |
| 2006/0058802 A1 | 3/2006 | Kofoed | |
| 2006/0195103 A1 | 8/2006 | Padget | |
| 2006/0241608 A1 | 10/2006 | Myerson | |
| 2007/0005071 A1 | 1/2007 | Kucklick | |
| 2007/0014649 A1 | 1/2007 | James | |
| 2007/0088362 A1 | 4/2007 | Bonutti | |
| 2007/0142838 A1 | 6/2007 | Jordan | |
| 2007/0156175 A1 | 7/2007 | Weadock | |
| 2007/0276388 A1 | 11/2007 | Robertson | |
| 2008/0093839 A1 | 4/2008 | Flynn et al. | |
| 2008/0131544 A1 | 6/2008 | Sander | |
| 2008/0161808 A1 | 7/2008 | Fox | |
| 2008/0161850 A1 | 7/2008 | Weisenburgh | |
| 2008/0177394 A1 * | 7/2008 | Chauhan | A61B 17/1677 623/20.18 |
| 2008/0287991 A1 | 11/2008 | Fromm | |
| 2009/0036931 A1 | 2/2009 | Pech | |
| 2009/0054903 A1 * | 2/2009 | Falahee | A61B 17/7064 606/104 |
| 2009/0093849 A1 | 4/2009 | Grabowski | |
| 2009/0149884 A1 | 6/2009 | Snyder | |
| 2009/0177203 A1 | 7/2009 | Reiley | |
| 2009/0254090 A1 | 10/2009 | Lizee | |
| 2009/0254130 A1 * | 10/2009 | Wotton, III | A61B 17/17 606/324 |
| 2009/0287259 A1 | 11/2009 | Trenhaile | |
| 2009/0306675 A1 * | 12/2009 | Wong | A61B 17/1703 606/96 |
| 2009/0306723 A1 | 12/2009 | Anapliotis | |
| 2009/0312802 A1 | 12/2009 | DaSilva | |
| 2009/0318980 A1 | 12/2009 | Falahee | |
| 2010/0016966 A1 | 1/2010 | Sander | |
| 2010/0036430 A1 | 2/2010 | Hartdegen | |
| 2010/0076487 A1 | 2/2010 | Ilahi | |
| 2010/0076490 A1 * | 3/2010 | Greenwald | A61B 17/7064 606/279 |
| 2010/0087859 A1 | 4/2010 | Jackson, Jr. | |
| 2010/0106194 A1 | 4/2010 | Bonutti | |
| 2010/0191332 A1 | 7/2010 | Euteneuer | |
| 2010/0241227 A1 | 9/2010 | Euteneuer | |
| 2010/0256687 A1 | 10/2010 | Neufeld | |
| 2011/0004221 A1 | 1/2011 | Euteneuer | |
| 2011/0009866 A1 | 1/2011 | Johnson | |
| 2011/0066194 A1 * | 3/2011 | Deffenbaugh | A61B 17/683 606/86 R |
| 2011/0087326 A1 | 4/2011 | Paulos | |
| 2011/0112558 A1 | 5/2011 | Whayne | |
| 2011/0137356 A1 | 6/2011 | Kollmer | |
| 2011/0166608 A1 * | 7/2011 | Duggal | A61B 17/683 606/320 |
| 2011/0224734 A1 | 9/2011 | Schelling | |
| 2011/0270278 A1 | 11/2011 | Overes | |
| 2011/0295324 A1 | 12/2011 | Donley | |
| 2012/0035613 A1 | 2/2012 | Falahee | |
| 2012/0059397 A1 | 3/2012 | Criscuolo | |
| 2012/0071566 A1 | 3/2012 | Kelly | |
| 2012/0071935 A1 | 3/2012 | Keith | |
| 2012/0109157 A1 | 5/2012 | Criscuolo | |
| 2012/0109215 A1 | 5/2012 | Ducharme | |

(56) References Cited

U.S. PATENT DOCUMENTS

| | | | |
|---|---|---|---|
| 2012/0116410 A1* | 5/2012 | Kortenbach | A61B 17/17 606/96 |
| 2012/0130374 A1 | 5/2012 | Bouduban | |
| 2012/0172936 A1 | 7/2012 | Horrell | |
| 2012/0184959 A1 | 7/2012 | Price | |
| 2012/0209334 A1 | 8/2012 | Lewis | |
| 2012/0245643 A1 | 9/2012 | Impellizzeri | |
| 2012/0277802 A1 | 11/2012 | Olms | |
| 2012/0303033 A1 | 11/2012 | Weiner | |
| 2013/0018424 A1 | 1/2013 | Subik | |
| 2013/0096559 A1 | 4/2013 | Katrana | |
| 2013/0123863 A1 | 5/2013 | Hollis | |
| 2013/0138154 A1 | 5/2013 | Reiley | |
| 2013/0144351 A1* | 6/2013 | Johnstone | A61B 17/17 606/86 R |
| 2013/0153627 A1 | 6/2013 | Euteneuer | |
| 2013/0153628 A1 | 6/2013 | Euteneuer | |
| 2013/0158661 A1 | 6/2013 | Euteneuer | |
| 2013/0165972 A1 | 6/2013 | Sullivan | |
| 2013/0172889 A1 | 7/2013 | Tyber | |
| 2013/0172942 A1 | 7/2013 | Lewis | |
| 2013/0226248 A1 | 8/2013 | Hatch | |
| 2013/0226252 A1 | 8/2013 | Mayer | |
| 2013/0231667 A1 | 9/2013 | Taylor | |
| 2013/0231669 A1* | 9/2013 | Sinnott | A61B 17/1714 606/79 |
| 2013/0240598 A1 | 9/2013 | Euteneuer | |
| 2013/0261670 A1 | 10/2013 | Laeng | |
| 2013/0261677 A1 | 10/2013 | Bouduban | |
| 2013/0267956 A1 | 10/2013 | Terrill | |
| 2013/0274769 A1 | 10/2013 | Bonutti | |
| 2014/0018809 A1 | 1/2014 | Allen | |
| 2014/0025112 A1 | 1/2014 | Bonutti | |
| 2014/0039561 A1 | 2/2014 | Weiner | |
| 2014/0066984 A1 | 3/2014 | Falahee | |
| 2014/0066995 A1 | 3/2014 | McCormick | |
| 2014/0066996 A1 | 3/2014 | Price | |
| 2014/0081327 A1 | 3/2014 | Lunn | |
| 2014/0094818 A1* | 4/2014 | Wallace | A61B 17/8866 606/96 |
| 2014/0097228 A1 | 4/2014 | Taylor | |
| 2014/0148859 A1 | 5/2014 | Taylor | |
| 2014/0194927 A1 | 7/2014 | Kaiser | |
| 2014/0249537 A1 | 9/2014 | Wong | |
| 2014/0309639 A1 | 10/2014 | Averous | |
| 2015/0080967 A1 | 3/2015 | DaSilva | |
| 2015/0112370 A1 | 4/2015 | Euteneuer | |
| 2015/0164564 A1 | 6/2015 | Reiley | |
| 2016/0089138 A1 | 3/2016 | Early | |
| 2016/0113770 A1 | 4/2016 | Early | |
| 2016/0192930 A1 | 7/2016 | Finley | |
| 2016/0242830 A1 | 8/2016 | Terrill | |
| 2016/0324555 A1 | 11/2016 | Brumfield et al. | |
| 2017/0119406 A1* | 5/2017 | Triplett | A61B 17/16 606/86 R |
| 2018/0110542 A1* | 4/2018 | DeVasConCellos | A61B 17/683 606/308 |

FOREIGN PATENT DOCUMENTS

| | | | |
|---|---|---|---|
| EP | 1952776 A1 | 8/2008 | |
| EP | 1707138 B1 | 5/2009 | |
| EP | 1927322 B1 | 6/2010 | |
| EP | 1707140 B1 | 9/2011 | |
| EP | 2606843 A1 | 6/2013 | |
| FR | 376911 A | 8/1907 | |
| FR | 551418 A | 4/1923 | |
| FR | 2928824 A1 | 9/2009 | |
| WO | 1998037825 A1 | 9/1998 | |
| WO | 2001019265 | 3/2001 | |
| WO | 2003075775 A1 | 9/2003 | |
| WO | 2007103333 A2 | 9/2007 | |
| WO | 2008149308 A1 | 12/2008 | |
| WO | 2010/019384 | 2/2010 | |
| WO | 2010094846 A1 | 8/2010 | |
| WO | 2010098820 A1 | 9/2010 | |
| WO | 2010098909 A1 | 9/2010 | |
| WO | 2010129156 A1 | 11/2010 | |
| WO | 2012033928 A1 | 3/2012 | |
| WO | 2012040862 A1 | 4/2012 | |
| WO | 2013006833 A1 | 1/2013 | |
| WO | 2013029600 A1 | 3/2013 | |
| WO | 2013131974 A1 | 9/2013 | |
| WO | 2013156545 A1 | 10/2013 | |
| WO | 2014084974 A1 | 6/2014 | |
| WO | 2014087111 A1 | 6/2014 | |
| WO | 2014127294 A1 | 8/2014 | |
| WO | 2016134160 A1 | 8/2016 | |

OTHER PUBLICATIONS

The Next Generation in Foot & Ankle Repair and Reconstruction Technology 2016, Arthrex, Inc., www.arthrex.com, 2016, 76 pp.

Speed Continuous Active Compression Implant, A120-031 Rev. 2, BioMedical Enterprises, www.bme-tx.com, 2014, 2 pp.

Lower Extremity Congruent Plating System, Acumed, www.acumed.net, Nov. 2008, 20 pp.

Acutrak Headless Compression Screw, Acumed, www.acumed.net, Apr. 2012, 20 pp.

Acumed Forefoot/Midfoot Plating System Surgical Technique, Acumed, LLC, www.acumed.net, 2014, 28 pp.

Acumed Locking Forefoot/Midfoot Plating System, Acumed, www.acumed.net, Sep. 2010, 20 pp.

Comprehensive Foot System, Arthrex, Inc., www.arthrex.com, 2013, 6 pp.

Comprehensive Solutions for Forefoot and Midfoot Surgery Using the Mini TightRope System, Athrex, Inc., www.arthrex.com, 2012, 15 pp.

Compression FT Screw System, Athrex, Inc., www.arthrex.com, 2014, 6 pp.

Distal Extremities Orthopaedic Update, Arthrex, Inc., www.arthrex.com, 2014, 24 pp.

Midfoot Plating Techniques Surgical Technique, Arthrex, Inc., www.arthrex.com, 2014, 14 pp.

Hallux Valgus Solutions, Arthrex, Inc., www.arthrex.com, 2009, 2 pp.

Lisfranc TightRope Fixation Surgical Technique, Arthrex, Inc., www.arthrex.com, 2013, 6 pp.

Low Profile MTP Plate Surgical Technique, Arthrex, Inc., www.arthrex.com, 2012, 4 pp.

Low Profile Plate and Screw System Surgical Technique, Arthrex, Inc., www.arthrex.com, 2012, 6 pp.

Plaple Fixation System Surgical Technique, Arthrex, Inc., www.arthrex.com, 2013, 4 pp.

QuickFix Staple System Surgical Technique, Arthrex, Inc., www.arthrex.com, 2010, 4 pp.

Distal Extremities Orthopedic Update, Arthrex, Inc., www.arthrex.com 2012, 24 pp.

O'Neill, P., et al., "Hallux Valgus Correction: A Comparison of IM Angle and 1st MTC Joint Pressure Before and After Correction", Arthrex, Inc., www.arthrex.com, 2008, 2 pp.

Foot & Ankle Repair and Reconstruction Technology Brochure, Arthrex, Inc., www.athrex.com, 2016, 86 pp.

Comprehensive Solutions for Forefoot and Midfoot Surgery Using the Mini TightRope System, Arthrex, Inc., www.arthrex.com, 2012, 15 pp.

Plantar Lapidus Plate Surgical Technique, Arthrex, Inc., www.arthrex.com, 2015, 6 pp.

A.L.P.S. Total Foot System Sales Sheet, Biomet Trauma, www.biomet.com, 2014, 10 pp.

Clover Staple, BioPro Biologically Oriented Prostheses, Brochure No. 19140, Rev. 1, 2 pp.

Dayton, Paul, et al., "Comparison of the Mechanical Characteristics of a Universal Small Biplane Plating Technique Without Compression Screw and Single Anatomic Plate with Compression Screw", The Journal of Foot & Ankle Surgery, www.jfas.org, 2016, pp. 1-5.

(56) References Cited

OTHER PUBLICATIONS

Foot Surgery Innovation in Forefoot Reconstruction, DePuy Orthopaedics, Inc., www.depuy.com, Aug. 2011, 36 pp.
DynaMX Compression Staple Technique Guide, MX Orthopedics, www.mxortho.com, 2 pp.
IntraOsseous Fixation Quick Reference Technique Guide, Extremity Medical, www.extremitymedical.com, 2 pp.
The Flower Akin Plate Procedure Guide, Flower Orthopedics, www.flowerortho.com, Apr. 2015, 8 pp.
Hallux Intramedullary Fusion Device Surgical Technique, Extremity Medical, www.extremitymedical.com, Sep. 2012, 12 pp.
I.B.S. Innovative Bone Synthesis Overview, Athrodax Healthcare International Ltd., www.arhrodax.co.uk, Oct. 2014, 4 pp.
Stapix Superelastic Nitinol Staple Fixation, Instratek Restore Surgical, LLC, www.instratek.com, 12 pp.
D.L.P. Dorsal Lisfranc Plate, Integra Lifesciences Corporation, www.integra-LS.com, 2007, 20 pp.
The IO Fix Advantage: Designed for Fusion, Extremity Medical, www.extremitymedical.com, 2012, 4 pp.
IO Fix Plus Intraosseous Fixation Surgical Technique, Extremity Medical, www.extremitymedical.com, 2012, 20 pp.
12 mm Memory Staples 20 mm Arthrodesis Memory Staples for Arthrodesis and Phalangeal Osteotomies, DePuy International Ltd., 2004, 4 pp.
Memory Staple Surgical Technique, DePuy Orthopaedics, Inc. 2006, 16 pp.
DynaMX Engineered Compression, MX Orthopedics., www.mxortho.com, 2 pp.
ALPS Total Foot System Product Rationale & Surgical Technique, DePuy Orthopaedics, Inc., 2011, 136 pp.
Re+Line Bunion Correction System Surgical Technique and Product Guide, Nextremity Solutions, nextremitysolutions.com, 2015, 9 pp.
Precision Ready Systems—Cortical Compression Staple System Case Report—Akin Osteotomy, Nextremity Solutions, 10 pp.
Forefoot Plating Systems, www.paragon28.com, 8 pp.
Precision Ready Systems—Surgical Technique and Product Guide, Nextremity Solutions, www.nextremitysolutions.com, 7 pp.
VLP Foot Variable—Angle Locked Plating System Surgical Technique, Smith & Nephew, www.smith-nephew.com, Mar. 2010, 28 pp.
Speed Shift Continuous Active Compression Implant, BioMedical Enterprises, www.bme-tx.com, 2 pp.
StaFIX Stainless Steel Staples, Small Bone Innovations, Inc., www.totalsmallbone.com, 2007, 2 pp.
2.4 mm/2.7 mm Variable Angle LCP Forefoot/Midfoot System—Procedure Specific Plates for Osteotomies, Fusions and Fractures of the Foot, Synthex (USA), www. synthes.com, Mar. 2011, 95 pp.
The Locking Calcaneal Plate. Part of the Synthes Small Fragment Locking Compression Plate (LCP) System. Synthes GmbH, www.depuysynthes.com, 2015, 20 pp.
Variable Angle LCP TMT Fusion Plates 2.4/2.7 Part of the Variable Angle LCP Forefoot/Midfoot System 2.4/2.7, DePuy Synthes, Synthes GmbH, www.depuysynthes.com, 2015, 36 pp.
2.4 mm/2.7 mm Variable Angle LCP Forefoot/Midfoot System. Procedure-Specific Plates for Osteotomies, Fusions and Fracturews of the Foot. Synthes (USA), www.synthes.com, 2010, 95 pp.
Biomechanical Comparison of a BIPLANAR Plate Construct to an Anatomic Plate with Compression Screw, Treace Medical Concepts, Inc., 2 pp.
TCP Total Compression Plate System, OrthoPro The Foot and Ankle Company, OrthoPro, LLC, www.orthoprollc.com, 4 pp.
Claw II, Polyaxial Compression Plating System with ORTHOLOC 3DSi Locking Screw Technology Surgical Technique Wright Medical Technology, Inc., www.wmt.com, 2011, 18 pp.
Charlotte Quick Staple, Wright Medical Technology, Inc., www.wmt.com, 2007, 2 pp.
Darco MFS, Locked Plating System for Reconstructive Forefoot Surgery, Wright Medical Technology, Inc., www.wmt.com, 2010, 8 pp.
FuseFORCE SuperElastic, Shape Memory Nitinol, Solana Surgical, www.solanasurgical.com, 4 pp.
European Search Report dated Sep. 30, 2019 for corresponding European Patent Application No. 16862724.8.

* cited by examiner

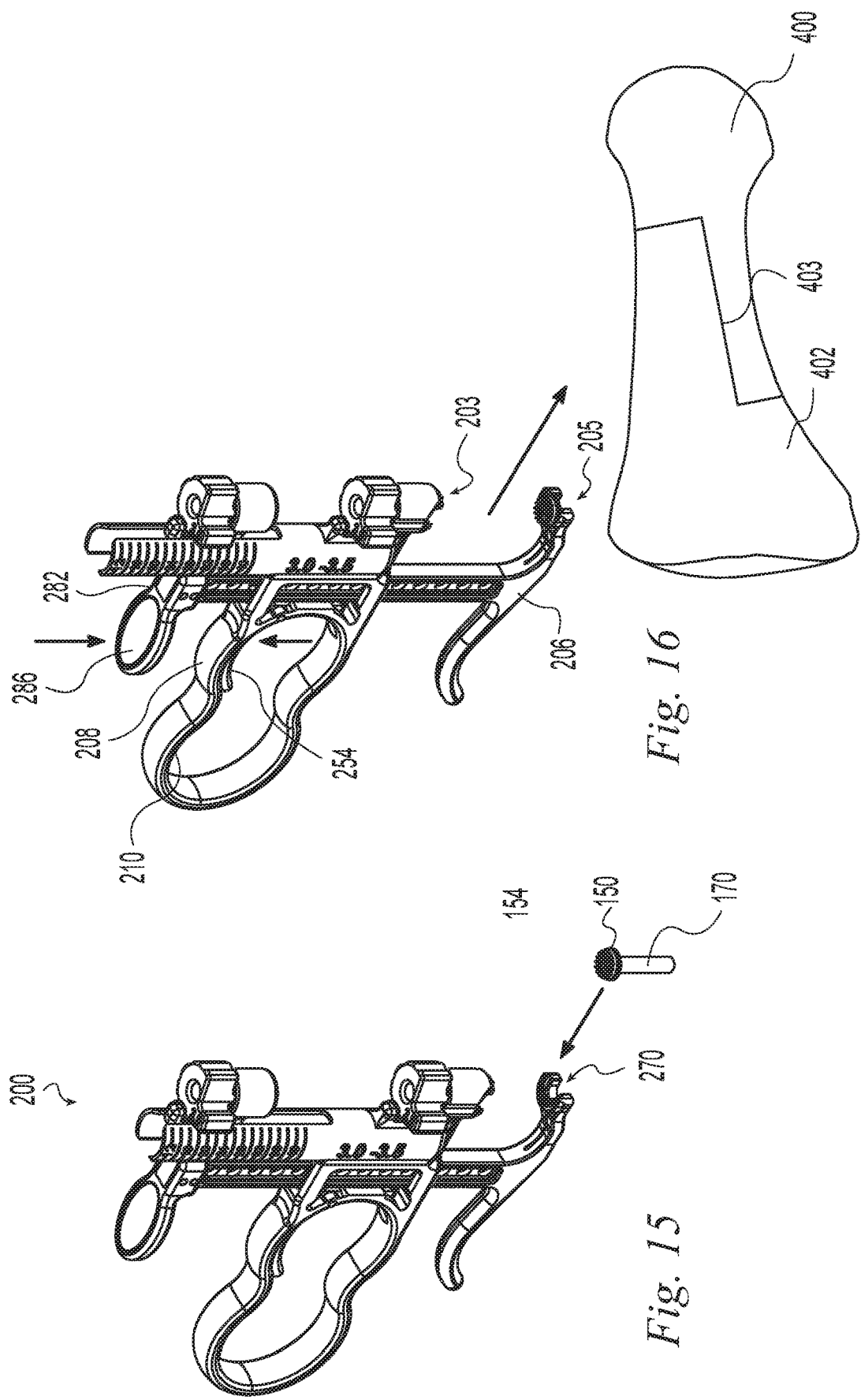

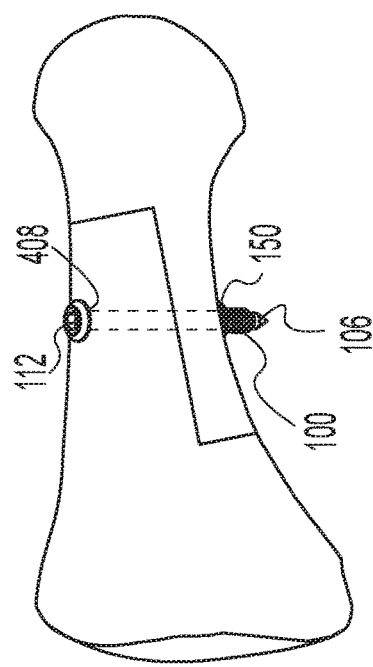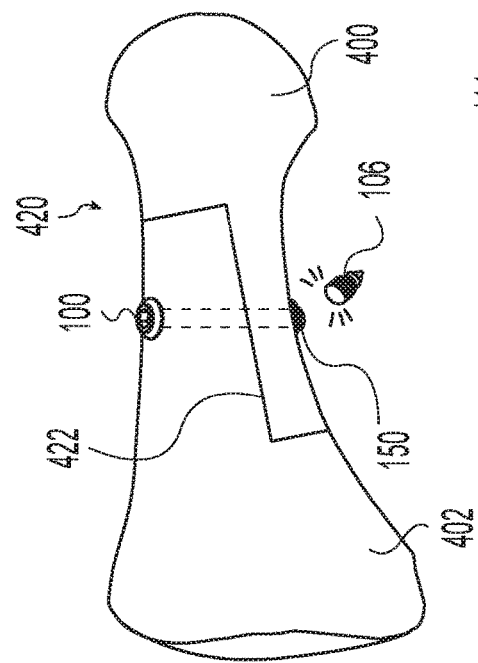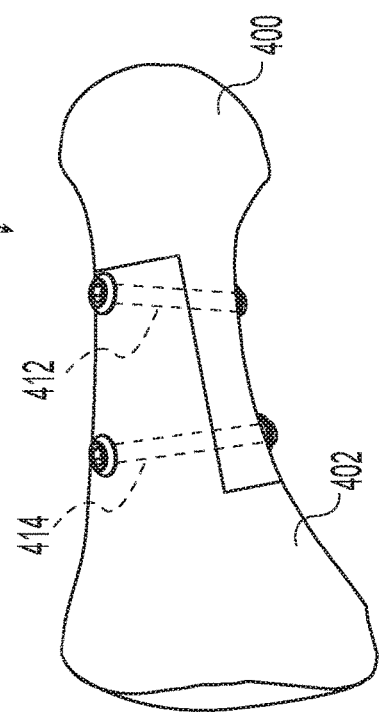

ORTHOPEDIC FASTENER, RETAINER, AND GUIDE

CROSS-REFERENCE TO RELATED APPLICATIONS

This application claims the benefit of U.S. Provisional Application No. 62/249,687, filed Nov. 2, 2015, which is hereby incorporated by reference.

FIELD OF THE INVENTION

Examples of the present invention relate generally to medical devices for connecting bone portions together and more particularly to fasteners and retainers connectable in axial force transmitting relationship and instruments for their installation.

BACKGROUND

Various conditions may affect skeletal joints such as the deterioration, elongation, shortening, or rupture of soft tissues, cartilage, and/or bone associated with the joint and consequent laxity, pain, and/or deformity. It may be desirable to change the angular alignment of a bone or a portion of a bone to restore function and/or reduce pain. It likewise may be desirable to fuse a joint to fix the bones of the joint in a better angular alignment or reduce pain caused by motion at the joint. It may also be desirable to support a fractured bone to allow healing of the fracture to occur. To this end, various osteotomy procedures, joint fusion procedures, fracture fixation procedures, implants and instruments have been proposed. Such procedures have been performed throughout the body to make various angular adjustments in, fuse joints associated with, and/or fuse fractures associated with tibia, fibula, femur, pelvis, humerus, ulna, radius, carpal, metacarpal, tarsal, metatarsal, phalangeal and other bones.

SUMMARY

Examples of the present invention provides medical devices for connecting bone portions together and more particularly to fasteners and retainers connectable in axial force transmitting relationship and guides for their installation.

In one example of the invention, a system operable to fix first and second bone portions relative to one another includes a retainer, a screw and a guide. The retainer has a receiver defining a receiver longitudinal axis. The screw is threadably engageable with the receiver and has a shaft portion defining a longitudinal axis. The shaft has a distal shaft width dimension perpendicular to the screw longitudinal axis in a width direction and a proximal shaft width dimension perpendicular to the screw longitudinal axis in the width direction. The proximal shaft width dimension is greater than the distal shaft width dimension. The guide has a handle, a bone contacting member mounted to the handle, and a retainer supporting member mounted to the handle opposite the bone contacting member. The retainer supporting member has a portion operable to releasably support the retainer opposite the bone contacting member. The bone contacting member and retainer supporting member are mounted for translation relative to one another and are resiliently biased toward one another. The guide is operable to clamp an object between the retainer and bone contacting member while the screw is engaged with the retainer.

In another example of the invention, a system for fixing first and second bone portions relative to one another includes a retainer, a fastener engageable with the retainer and a guide. The guide includes a handle, a bone contacting member mounted to the handle, and a retainer supporting member mounted to the handle opposite the bone contacting member. The retainer supporting member has a portion operable to releasably support the retainer opposite the bone contacting member. The bone contacting member and retainer supporting member are mounted for translation relative to one another. The retainer supporting member has a first grip and a second grip such that pressing the first grip and the handle toward one another moves the bone contacting member and retainer supporting member away from one another and pressing the second grip and the handle toward one another moves the bone contacting member and retainer supporting member toward one another.

In another example of the invention, a system for fixing first and second bone portions relative to one another includes a retainer, a screw threadably engageable with the retainer, and a guide. The guide has a bone contacting portion and an opposed retainer supporting portion operable to releasably retain the retainer opposite the bone contacting portion. The bone contacting portion and retainer supporting portion define a motion axis and are mounted for axial translation parallel to the motion axis toward and away from one another. The retainer supporting portion includes spaced apart arms defining a perimeter greater than one half a perimeter of the retainer. The arms are operable to spread apart to receive the retainer as the retainer is pressed between the arms and spring back to positively grip the retainer.

BRIEF DESCRIPTION OF THE DRAWINGS

Various examples of the present invention will be discussed with reference to the appended drawings. These drawings depict only illustrative examples of the invention and are not to be considered limiting of its scope.

FIGS. 15-23 a perspective views of a method of using the implants and instruments of FIGS. 1-14 according to one example of the invention;

DESCRIPTION OF THE ILLUSTRATIVE EXAMPLES

Figure 1:
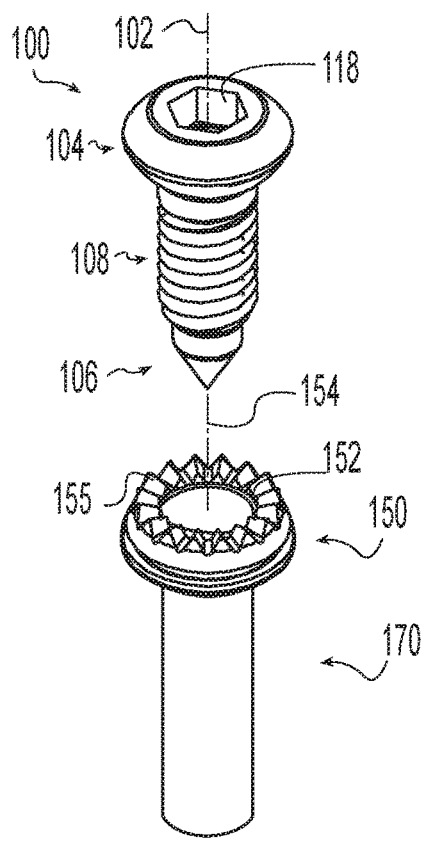
FIG. 1 is a perspective view of a fastener and retainer according to one example of the invention.
Figure 2:
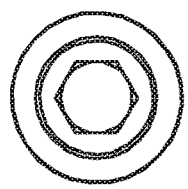
FIG. 2 is a top view of the fastener of FIG. 1.
Figure 3:
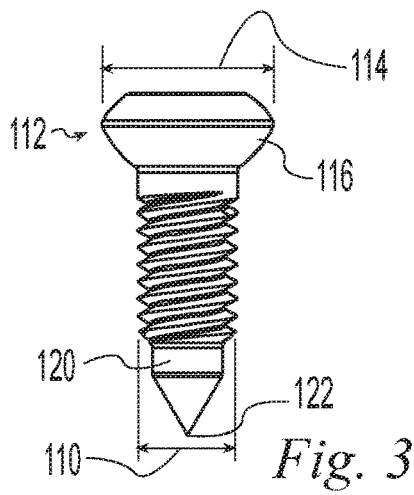
FIG. 3 is a front view of the fastener of FIG. 1.
Figure 4:
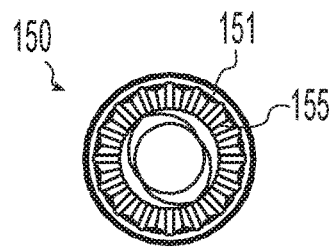
FIG. 4 is a top view of the retainer of FIG. 1.
Figure 5:
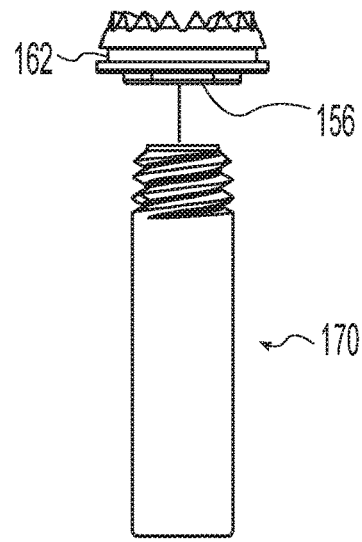
FIG. 5 is a front view of the retainer of FIG. 1.
Figure 6:
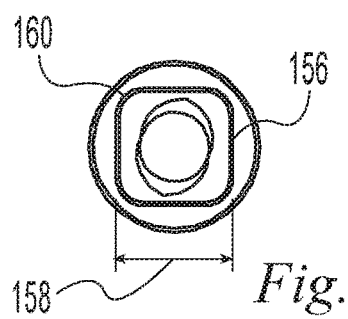
FIG. 6 is a bottom view of the retainer of FIG. 1.
Figure 7:
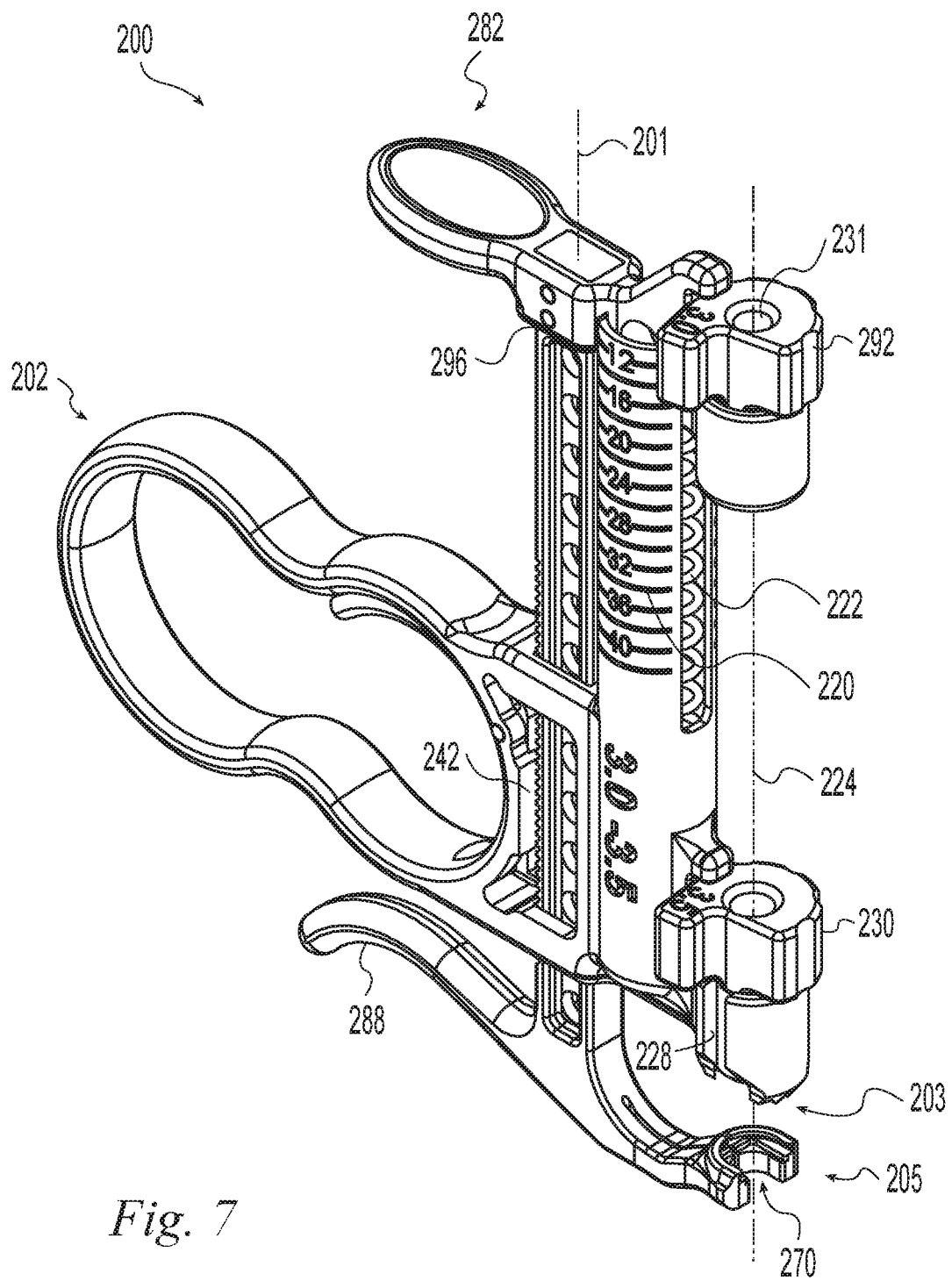
FIG. 7 is a perspective view of a guide according to one example of the invention.
Figure 8:
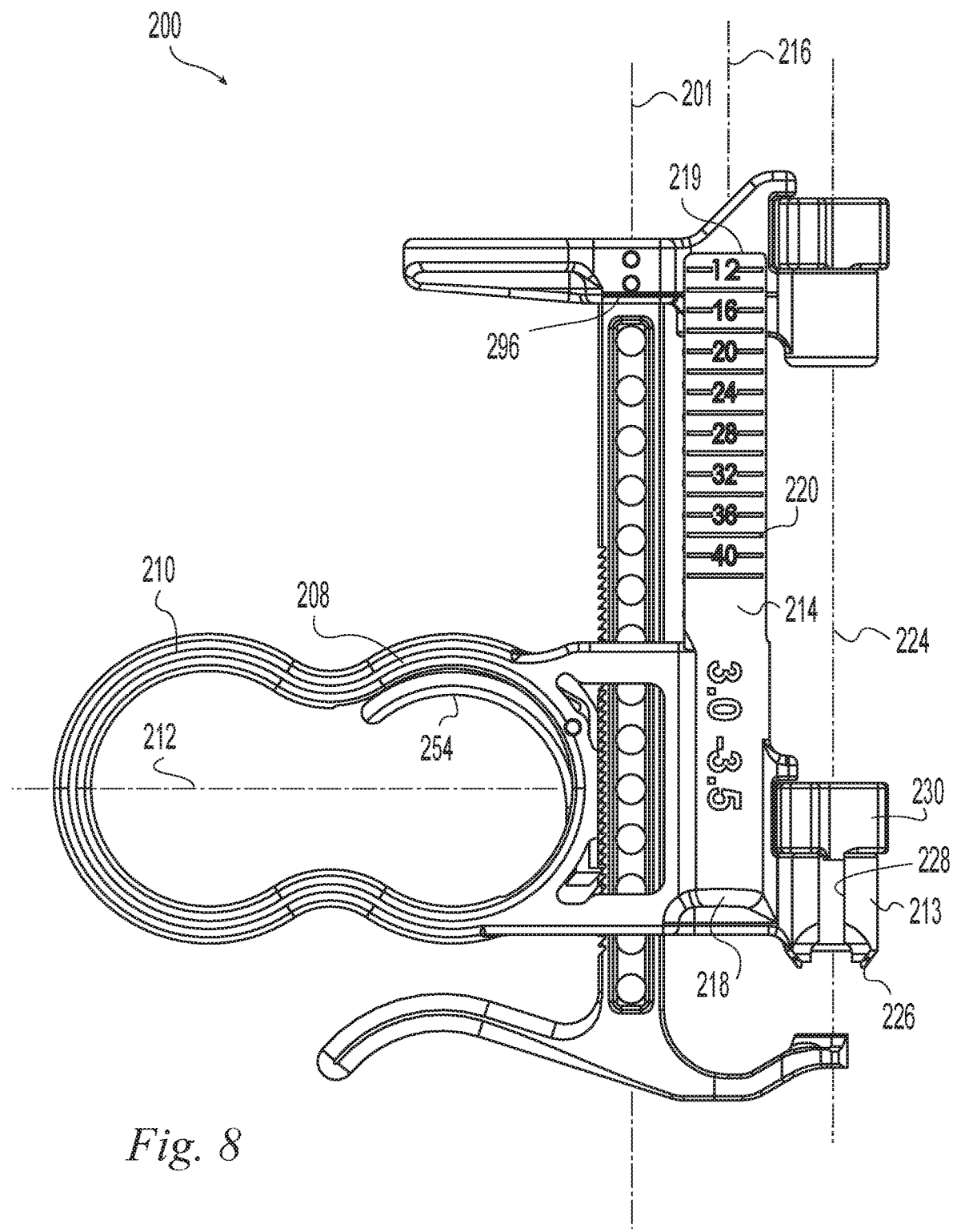
FIG. 8 is a side view of the guide of FIG. 7.
Figure 9:
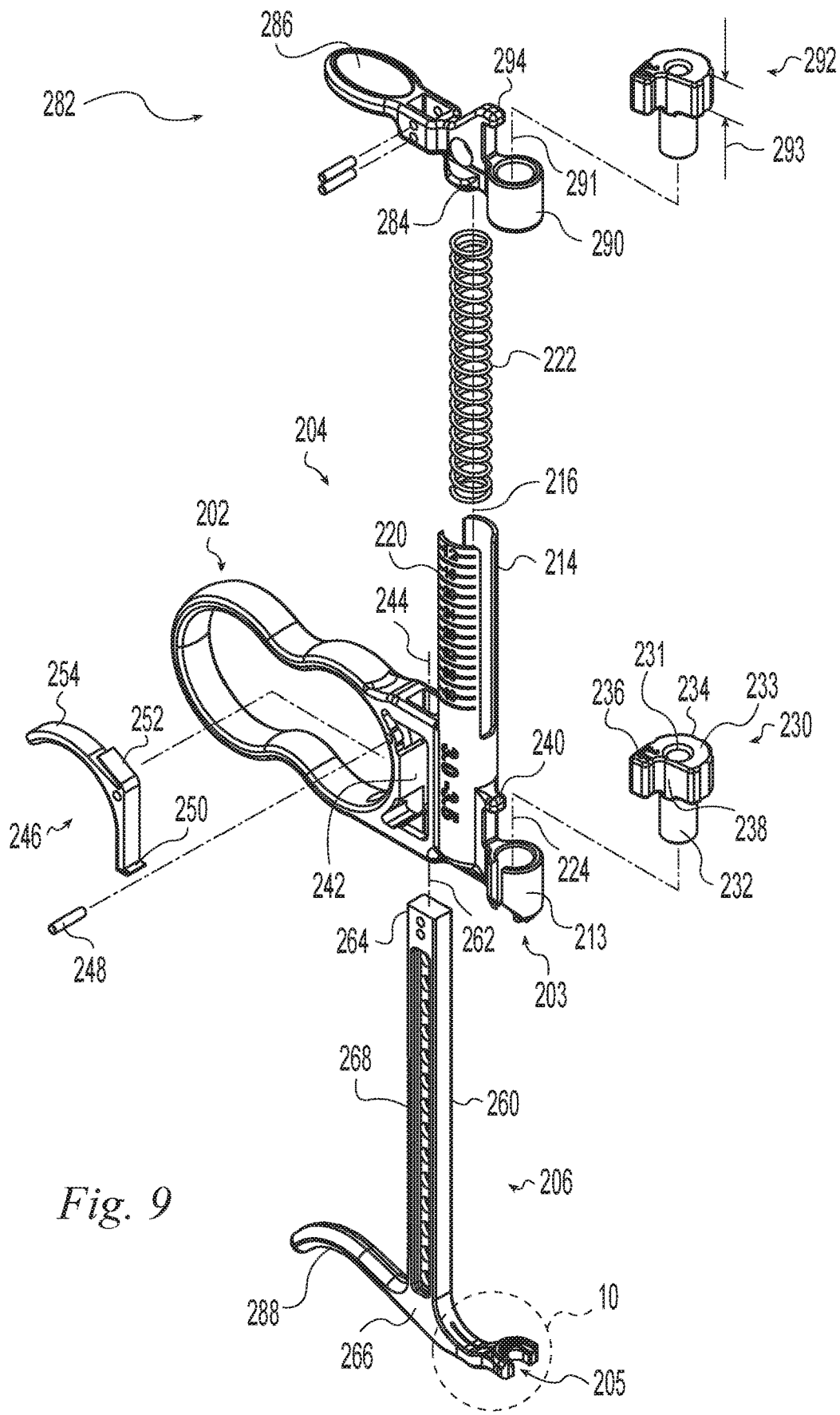
FIG. 9 is an exploded perspective view of the guide of FIG. 7.
Figure 10:
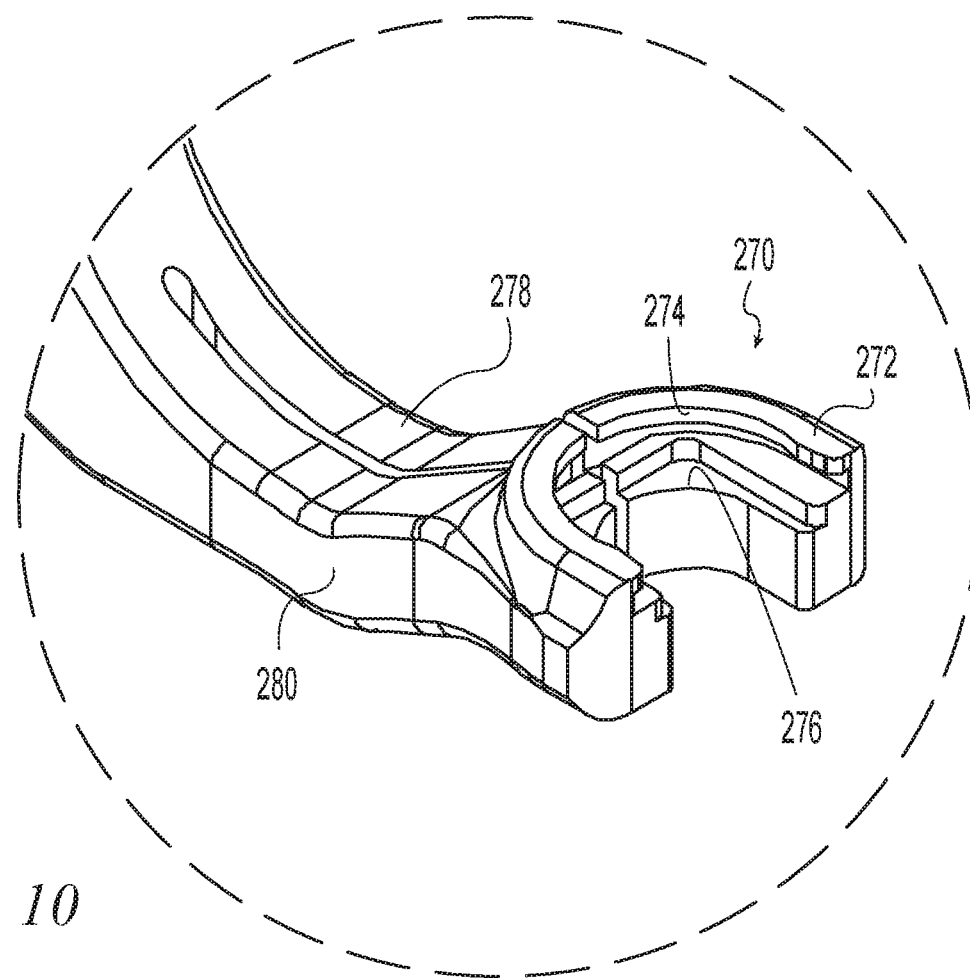
FIG. 10 is a detail perspective view of a portion of the guide of FIG. 7.
Figure 11:
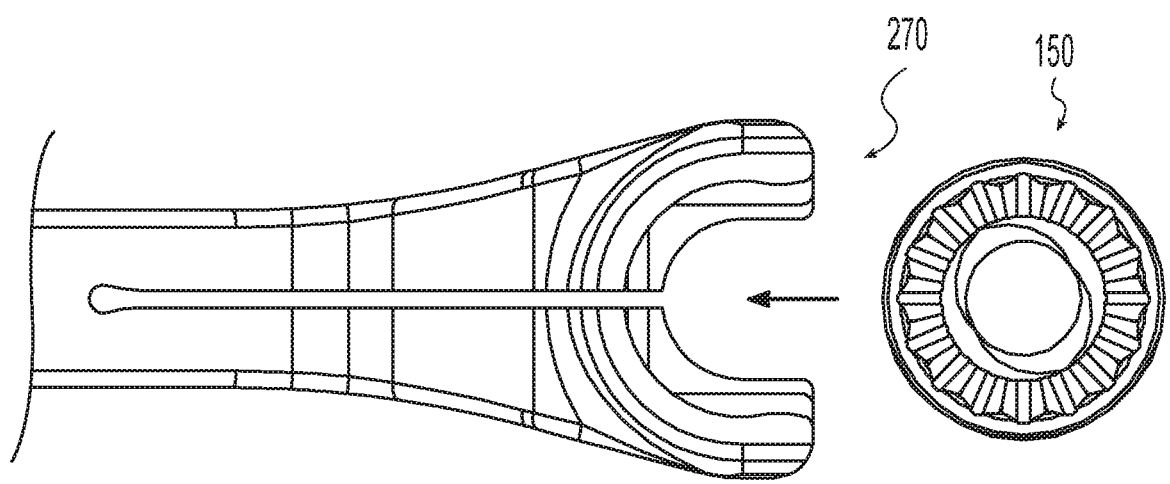
FIG. 11 is a detail top view of the portion of the guide of FIG. 10 shown receiving the retainer of FIG. 1.

The following illustrative examples describe methods, implants, and instruments for connecting bone portions together and more particularly to fasteners and retainers connectable in axial force transmitting relationship and instruments for their installation. The bone portions may be portions of the same bone that have become separated due to a fracture or a cut. The bone portions may be portions of different bones. In particular, the methods, implants, and instruments are particularly well suited to joining bone portions such as portions separated due to fractures or osteotomies or in an arthrodesis performed to fuse a joint. The invention may be used on any bone or joint including but not limited to bones such as a tibia, fibula, femur, pelvis, humerus, ulna, radius, carpal, metacarpal, tarsal, metatarsal, phalange and joints associated therewith. The term "transverse" is used herein to mean crossing as in non-parallel and includes but is not limited to perpendicular.

FIGS. 1-6 illustrate a fastener 100 and mating retainer 150 according to one example of the invention. The fastener has a longitudinal axis 102 extending between a proximal end 104 and a distal end 106. The retainer 150 includes a receiver 152 having a receiver longitudinal axis 154. In the illustrative example of FIGS. 1-6, the fastener 100 is coaxially engageable with the retainer 150 in axial force transmitting relationship along the fastener and receiver longitudinal axes 102, 154. The fastener 100 is engageable with the retainer 150 in a first direction along the receiver longitudinal axis and the engagement resists translation of the fastener 100 away from the retainer 150 in a second direction along the fastener and receiver longitudinal axes opposite the first direction. In the illustrative example of FIGS. 1-6, the fastener includes a shaft portion 108 with a shaft width dimension 110 perpendicular to the fastener longitudinal axis in a width direction. The fastener further includes a head 112 at the proximal end 104 having a head width dimension 114 perpendicular to the fastener longitudinal axis in the width direction. The head width 114 is greater than the shaft width 110. In the illustrative example of FIGS. 1-6, the fastener 100 is in the form of a screw with a threaded shaft 108 and the retainer 150 is in the form of a nut with a threaded receiver 152 for receiving the threaded shaft in threaded engagement. The head 112 includes a tapered bottom surface 116 receivable in a countersink formed in a bone surface. The head further includes a socket 118 for engaging a driver to rotate the screw into engagement with the retainer 150. The distal end 106 of the fastener includes a smooth portion 120 with a diameter equal to or slightly less than the minor diameter of the female threads in the receiver 152 and is further tapered distally to a point 122. In use, the point 122 enters the retainer threads first followed by the smooth portion 120 to axially align the fastener and retainer to facilitate thread engagement and to avoid cross threading.

In the illustrative example of FIGS. 1-6, the retainer 150 includes a plurality of axially projecting teeth 155 formed on a first, proximal, bone engaging side 151 to aid in gripping the bone. The retainer 150 includes a counter torque coupling 156 formed on a second, distal side. In the illustrative example of FIGS. 1-6, the counter torque coupling is a polygonal projection engageable with a guide for resisting rotation of the retainer 150 as the fastener 100 is engaged with the retainer. The torque coupling has a width 158, e.g. the distance between sides, and radiused vertices 160 between the sides. The radii of the vertices preferably are chosen so that the torque coupling self-aligns when it is pressed sideways, e.g. normal to the receiver axis 154, into an engaging polygonal feature on a guide. In other words, the radii are chosen to be sufficiently large so that a misaligned torque coupling will rotate into alignment as it is pressed into a receiving feature but sufficiently small so that once engaged, there is sufficient flat side engagement to transmit the required torque. Preferably, the radii of the vertices are in the range of 15-35 percent of the width 158. More preferably the radii are in the range of 20-30 percent of the width 158. In the illustrative example of FIGS. 1-6, the torque coupling is a square projection having radiused vertices 160 with radii approximately 25 percent of the width 158. The retainer 150 is also engageable with a guide in tongue and groove fashion to resist translation of the retainer along the receiver longitudinal axis. In the illustrative example of FIGS. 1-6, the retainer 150 includes an external circumferential groove 162 engageable with a tongue on a guide. In the illustrative example of FIGS. 1-6, the fastener 100 and retainer 150 are provided with a multi-lead thread, e.g. a double lead thread. It has been found by the present inventors that the engagement of the double lead male thread of the fastener 100 with the double lead female thread of the receiver 150 provides tactile feedback similar to that of a bone screw threaded into bone. Surgeons are familiar with installing bone screws into bone and the tactile sense for when the proper torque has been applied. Typical machine screw threads used with bolts and nuts are finer pitch than bone screw threads and consequently generate more mechanical advantage. For the same tactile feedback as bone screws, typical machine screws generate too much compressive force. By using a dual lead thread, thread strength is maintained while reducing the mechanical advantage and thus producing a familiar tactile feedback at an appropriate compression level.

A retainer handle 170 may be provided to facilitate storage, retrieval, and handling of the retainer 150. The handle 170 is releasably engageable with the retainer such that the handle may be used to position the retainer 150 and then may be removed. The handle may engage the retainer in a press fit, snap fit, tongue and groove arrangement, threaded engagement, or other suitable engagement. Preferably the handle 170 is engageable with the retainer in a direction orthogonal to the direction in which the retainer engages a guide. For example, if the retainer engages a guide radially, it is preferable that the handle 170 engage the retainer 150 axially such that forces generated in engaging the retainer 150 with the guide 200 do not tend to disengage the handle 170. This is especially true if the handle engages in a press fit arrangement. Where the handle 170 engages the retainer 150 axially, it is preferable that the handle 170 be engageable in an axial direction with the second side of the retainer 150 or in other words opposite the side from which the fastener engages the retainer. In the illustrative example of FIGS. 1-6, the retainer handle 170 engages the retainer axially in a threaded engagement. The retainer handle 170 may be threaded into the retainer from either side but is preferably threaded into the second side so that it may be readily removed after the retainer 150 is engaged with a guide.

While the illustrative example of FIGS. 1-6 have shown a screw and nut, the fastener and retainer engagement may take many other forms including for example, partial turn engagements, ratcheting engagements like a cable tie, snap lock engagements, and other suitable axial force transmitting engagements.

FIGS. 7-11 illustrate a guide 200 usable with the fastener and retainer of FIGS. 1-6 according to one example of the invention. The guide 200 includes a bone contacting portion 203 and a retainer supporting portion 205 opposite the bone contacting portion. The bone contacting portion and retainer supporting portion are mounted for axial translation parallel to a motion axis 201 toward and away from one another in a clamping arrangement.

In the illustrative example of FIGS. 7-11, the bone contacting portion 203 is part of a bone contacting member 204 (FIG. 9) and the retainer supporting portion 205 is part of a separate and opposed retainer supporting member 206. The retainer supporting portion 205 is configured to releasably support the retainer 150 opposite the bone contacting portion 203 with the receiver axis 154 in predetermined relationship to the guide 200. The guide 200 is configured to guide a drill coaxial with the receiver axis 154 and to allow passage of a fastener 100 coaxial with the receiver axis 154 into engagement with the retainer 150 while the guide remains in clamping engagement with the bone.

In the illustrative example of FIGS. 7-11, the bone contacting member 204 includes a handle 202 having first and second finger loops 208, 210 (FIG. 8) having a longitudinal axis 212 and inner and outer gripping surfaces. A spring tube 214 is fixed to the handle 202 and has a longitudinal axis 216 extending transverse to the finger loop axis 212 and parallel to the motion axis 201. The distal end 218 of the spring tube is at least partly closed to provide a distal stop for containing a spring. The proximal end 219 of the spring tube is at least partly open to receive a portion of the retainer supporting member. The outside of the spring tube 214 includes indicia 220 indicating the recommended length of fastener 100 corresponding to different distances between the bone contacting portion 203 and retainer supporting portion 205. A main spring 222 is disposed in the spring tube 214. A guide tube 213 is fixed to the spring tube 214 and defines a longitudinal axis 224 extending between an open distal end and an open proximal end. The bone contacting portion 203 is formed on the distal end of the guide tube 213 and includes a plurality of teeth 226 to enhance the grip of the guide 200 on a bone surface. A slot 228 in the side of the guide tube 213 permits access to a screw head if needed. For example, a pair of forceps or a probe may be inserted through the slot to remove a screw that is the wrong size.

In the illustrative example of FIGS. 7-11, a guide tube reducer 230 is receivable in the guide tube 213 to reduce the inner diameter of the guide tube 213 from the inner diameter of the guide tube to the diameter of the bore 231 in the guide tube reducer 230. For example the guide tube reducer 230 may be used for guiding a drill in the bore 231 and then removed to permit passage of another tool or fastener having a portion with a larger diameter than the drill. The guide tube reducer 230 has a cylindrical portion 232 sized for a slip fit within the guide tube 213 and an enlarged head 234. The head 234 has a semi-circular portion 233 and an arm 236 extending from the semi-circular portion 233 forming a notch 238 between the arm 236 and semi-circular portion 233. The guide tube reducer 230 is placed in the guide tube 213 with the notch 238 facing the spring tube 214 to clear a tab 240 projecting from the spring tube 214. Once the guide tube reducer 230 is seated in the guide tube 213, the head 234 is rotated so that the semi-circular portion 233 of the head is under the tab 240. The arm 236 provides extra leverage, if needed, for rotating the guide tube reducer 230 and rotates into contact with the spring tube 214 to serve as a rotation stop. The position of the tab 240 overlying the head 234 retains the guide tube reducer 230 in the guide tube 213. To remove the guide tube reducer 230, it is rotated until the notch 238 is aligned with the tab 240 and then withdrawn axially.

In the illustrative example of FIGS. 7-11, the bone contacting member 204 includes a passage 242 (FIG. 9) having a longitudinal axis 244 parallel to the motion axis 201 for receiving the retainer supporting member 206 for axial translation. A pawl 246 is mounted to the handle 202 for rotation about a pivot pin 248. A free end 250 of the pawl is extendable within the passage 242. A cantilevered spring 252 extends from the pawl and presses against the handle to bias the free end 250 into a first position toward the passage axis 244. An actuator 254 extends from the pawl and extends into the first finger loop 208. The actuator 254 is curved to follow the contour of the upper inner surface of the first finger loop 208. Upward pressure on the actuator 254 overcomes the force of the spring 252 and pivots the pawl into a second position in which the free end 250 is pivoted away from the passage axis 244.

In the illustrative example of FIGS. 7-11, the retainer supporting member 206 includes an elongated body 260 defining a longitudinal axis 262 extending between a proximal end 264 and a distal end 266. The body 260 is sized and shaped to engage the passage 242 in axial translating relationship. A rack 268 is formed on a side of the body 260 facing the free end 250 of the pawl 246. The retainer supporting portion 205 extends from the retainer supporting member 206 and forms a seat 270 (FIG. 10) operable to receive the retainer 150. Preferably the seat 270 receives the retainer 150 in a direction transverse to the receiver longitudinal axis 154. In the illustrative example of FIGS. 7-11, the seat 270 includes a tongue 272 receivable within the groove 162 of the retainer 150 to restrain the retainer from movement parallel to the receiver longitudinal axis 154. The tongue defines a perimeter 274 that extends more than one half the perimeter of the groove 162 of the retainer so that the tongue 272 engages the groove 162 in snap-fit relationship for positive retention of the retainer.

In the illustrative example of FIGS. 7-11, the retainer 150 and seat 270 engage in torque transmitting relationship that resists rotation of the retainer 150 as the fastener 100 is engaged with the retainer 150. The seat 270 includes a recess 276 complimentary in shape to and able to receive the counter torque coupling 156 of the retainer 150. The seat 270 is split to form a pair of opposed resilient arms 278, 280 that flex outwardly as the retainer is inserted into the seat such that they resiliently grip the retainer 150.

In the illustrative example of FIGS. 7-11, a cap 282 is fixed to the proximal end 264 of the elongated body 260. The cap 282 includes a spring follower 284 received in the spring tube 214 against which the main spring 222 presses to bias the retainer supporting member 206 proximally (upwardly) so that the retainer supporting portion 205 is biased toward the bone contacting portion 203. The cap 282 includes a finger grip 286 extending above the handle 202. The finger grip 286 is engageable by a user and pressable toward the handle in a squeezing motion to oppose the spring bias and move the retainer supporting portion 205 away from the bone contacting portion 203. Another finger grip 288 extends from the distal end 266 of the elongated body 260 below the handle 202. The finger grip 288 is engageable by a user and pressable toward the handle to move the retainer supporting portion 205 toward the bone contacting portion 203. A cap guide tube 290 is fixed to the cap 282 and defines a longitudinal axis 291 coaxial with the longitudinal axis 224 of the handle guide tube 213. A cap guide tube reducer 292 configured like the handle guide tube reducer 230 is engageable in similar manner with the cap guide tube 290 including retention by tab 294. The guide tube reducers 292 and 230 may be identical. The cap guide tube reducer 292 has a thickness 293 above the guide tube 290. The cap 282 further includes an index mark 296 (FIG. 8) readable relative to the indicia 220 of the spring tube 214 to indicate a recommended length of fastener 100 corresponding to different distances between the bone contacting portion 203 and retainer supporting portion 205.

Figures 12, 13, 14:
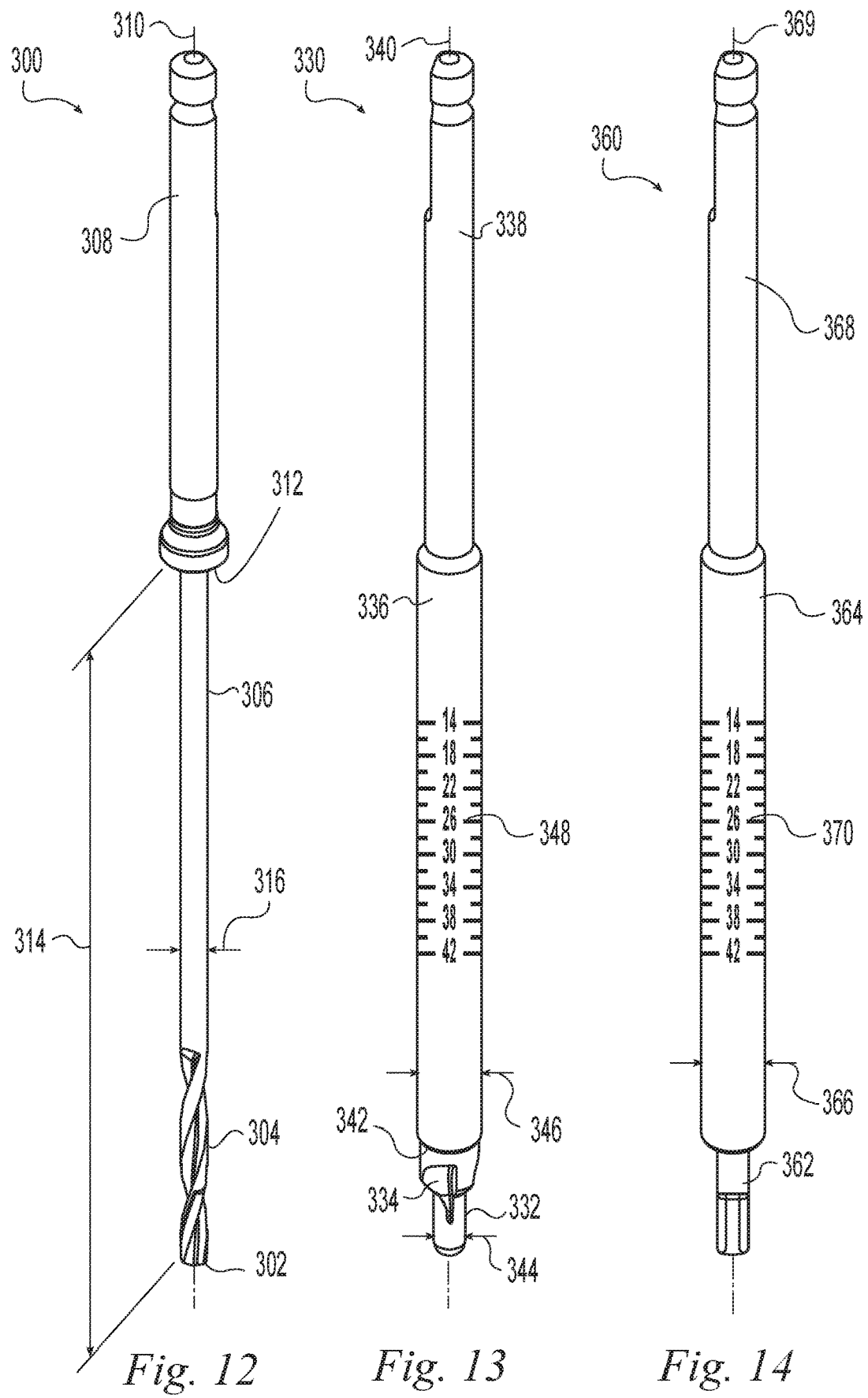
FIG. 12 is a perspective view of a drill according to one example of the invention.
FIG. 13 is a perspective view of a countersink according to one example of the invention.
FIG. 14 is a perspective view of a driver according to one example of the invention.

FIGS. 12-14 illustrate instruments useable with the guide and implants of FIGS. 1-11 according to one example of the invention. FIG. 12 depicts an illustrative example of a drill 300 having a distal cutting tip 302, flutes 304, a smooth shank portion 306, a proximal drive connection 308, and a longitudinal axis 310 extending between the proximal and distal ends. A shoulder 312 at the junction of the shank 306 and drive connection 308 may be used as a depth stop. The portion of the drill 300 distal of the shoulder 312 has a length 314. The portion of the drill 300 distal of the shoulder has a diameter 316 sized to slip fit within the bore 231 of the guide tube reducer 230.

FIG. 13 depicts an illustrative example of a counter sink 330 having a distal cylindrical guide point 332, cutting flutes 334, a smooth shank 336, a proximal drive connection 338, and a longitudinal axis 340 extending between the proximal and distal ends. A shoulder 342 at the distal end of the shank 336 may be used as a depth stop. The guide point 332 has a diameter 344 sized for a slip fit in a hole drilled with the drill 300. The shank 336 has a diameter 346. A scale 348 is inscribed on the shank 336.

FIG. 14 depicts an illustrative example of a fastener driver 360 having a distal driver portion 362 engageable with the socket 118 of the fastener 100, e.g. a polygonal drive extension engageable with a polygonal socket for torque transmission, a shank 364 having a shank diameter 366, a proximal drive connection 368, and a longitudinal axis 369. A scale 370 is inscribed on the shank 364.

FIGS. 15-23 illustrate a method of using the implants and instruments of FIGS. 1-14 according to one example of the invention.

In FIG. 15, the retainer 150 is manipulated with the attached handle 170 and is pressed laterally, transverse to the receiver axis 154, into the seat 270 of the guide 200. After the retainer 150 is seated, the handle 170 is removed distally along the receiver axis.

In FIG. 16, a user places fingers in the finger loops 208, 210 and presses the finger loops and the finger grip 286 of the cap 282 together. With the guide gripped in this manner, the user's finger naturally rests on the actuator 254 and pressing the finger loops and the finger grip 286 together produces upward pressure on the actuator 254 and pivots the pawl 246 into the second position in which it is disengaged from the rack 268. Further pressing moves the retainer supporting member 206 distally relative to the handle and increases the space between the retainer supporting portion 205 and the bone contacting portion 203 so that one or more bone portions may be received between them such as, for example, bone portions 400 and 402 created by a corrective osteotomy 403. The arrangement of the actuator 254 within the handle causes the pawl 246 to disengage from the rack 268 as a natural consequence of pressing the finger loops 208, 210 and finger grip 286 together so that no additional unlocking step or other deliberate action by the user is required.

Figure 17:
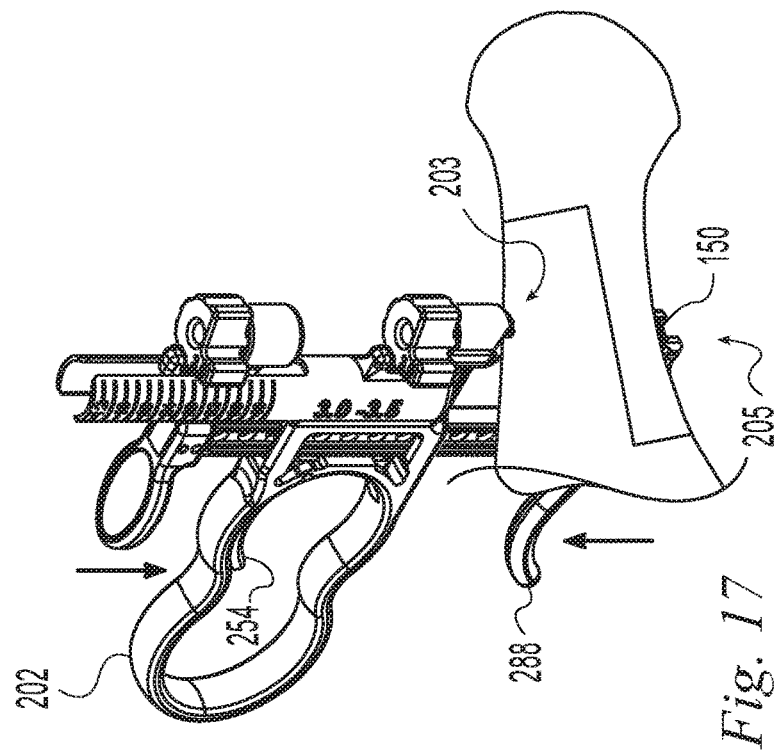

In FIG. 17, the guide has been placed over the bone portions 400, 402 and the pressure on the finger loops 208, 210 and finger grip 286 has been reduced so that the main spring 222 moves the retainer supporting member 206 proximally relative to the handle to move the retainer supporting portion 205 toward the bone contacting portion 203 so that the bone contacting portion 203 and the retainer 150 supported on the retainer supporting member 206 act as jaws to grip the bone with a first compressive force. Also, with pressure reduced on the actuator 254, the pawl spring 252 biases the pawl into the first position in which it engages the rack 268 and prevents the retainer supporting portion 205 and the bone contacting portion 203 from moving apart and releasing the bone portions 400, 402. If additional compression is desired on the bone portions 400, 402, the user may grip the distal finger grip 288 and the handle 202, e.g. the outer upper surface of the finger loops or the lower inner surface of the finger loops, and press them toward one another. The pressure applied by the user will generate a second compressive force, greater than the first compressive force generated by the main spring alone. This additional force results in the retainer 150 moving closer to the bone contacting portion 203 as they grip the bone even tighter. The pawl 246 ratchets over the teeth on the rack 268 to allow motion in this first rack direction and engages the teeth to prevent motion in the opposite, or second, rack direction.

Figure 18:
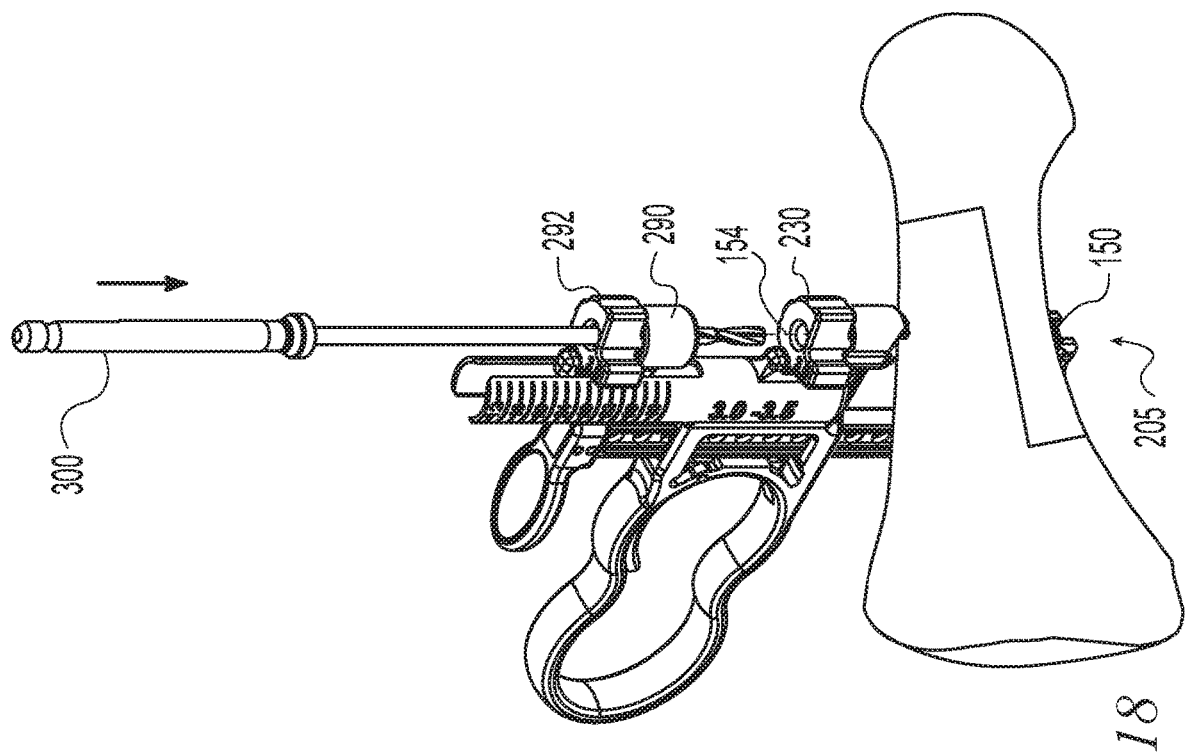

In FIG. 18, the drill 300 is guided in the guide tube reducers 292, 230 coaxial to the receiver axis 154 to form a hole 406 (FIG. 19) through the bone portions. The proximal cap guide tube 290 is rigidly linked to the retainer supporting portion 205 and the cap guide tube reducer 292 has a predetermined thickness 293. The drill 300 has a predetermined length 314 below the shoulder 312 sized so that with the shoulder 312 abutting the top of the cap guide tube reducer 292 the distal cutting tip 302 of the drill will reach, but not extend through, the retainer 150 as it is supported on the retainer supporting portion 205 and pressed against the bone.

Figure 19:
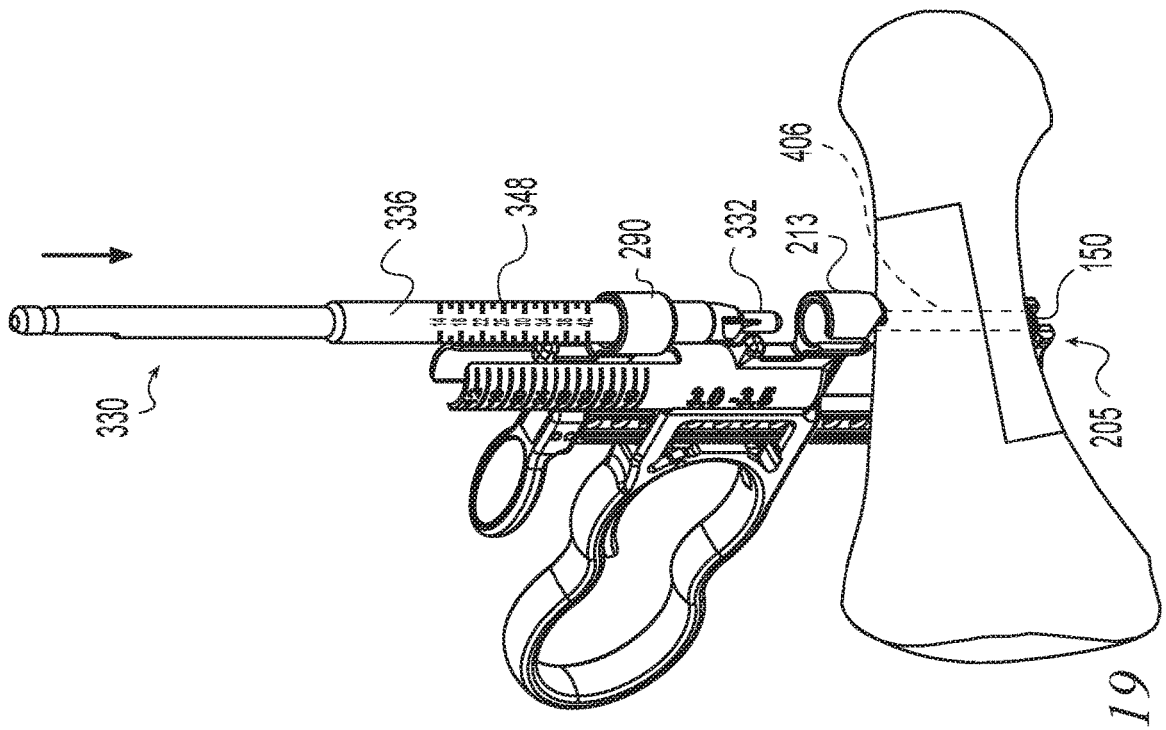
Figure 24:
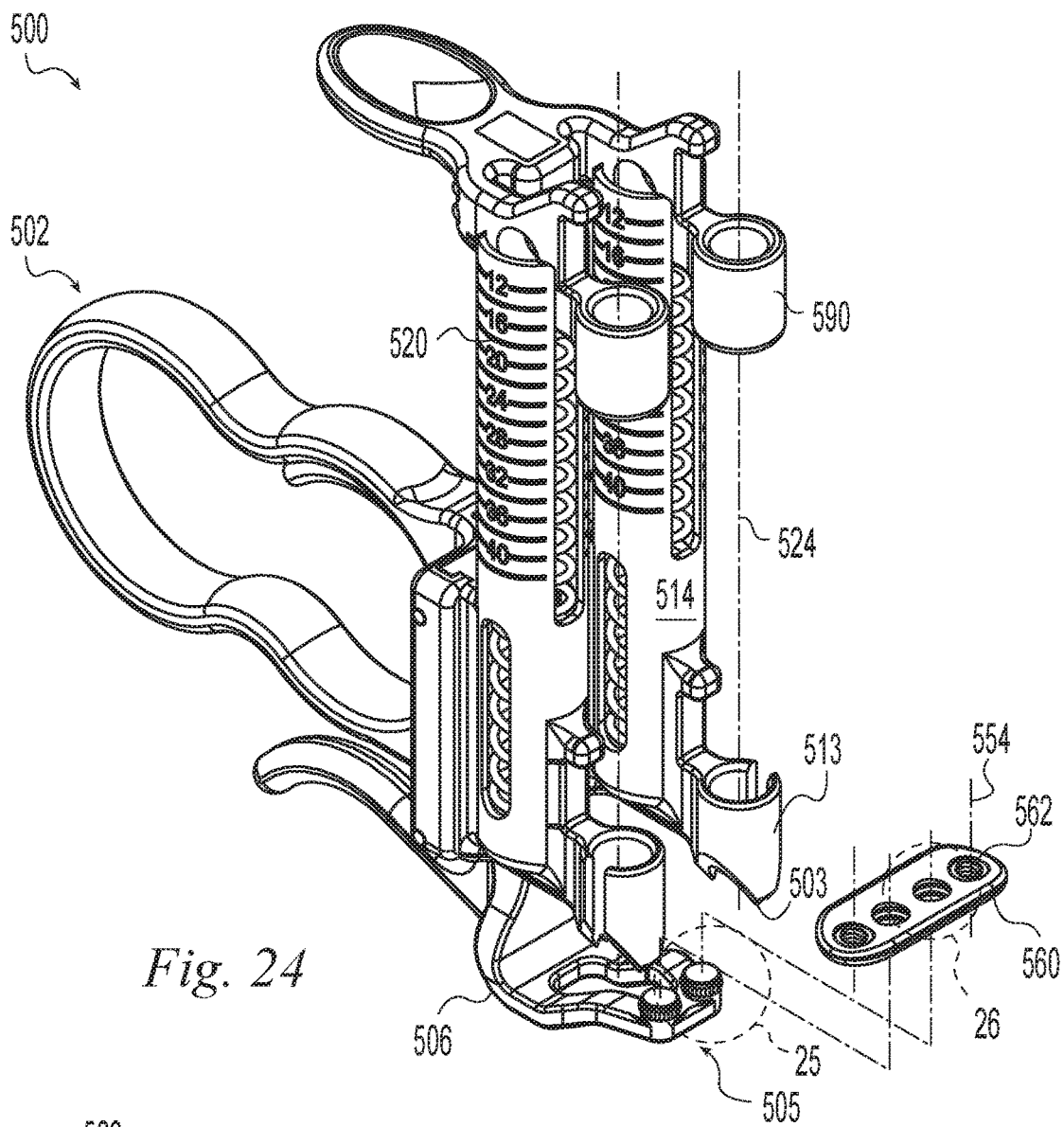
FIG. 24 is a perspective view of a guide and retainer according to one example of the invention.
Figure 25:
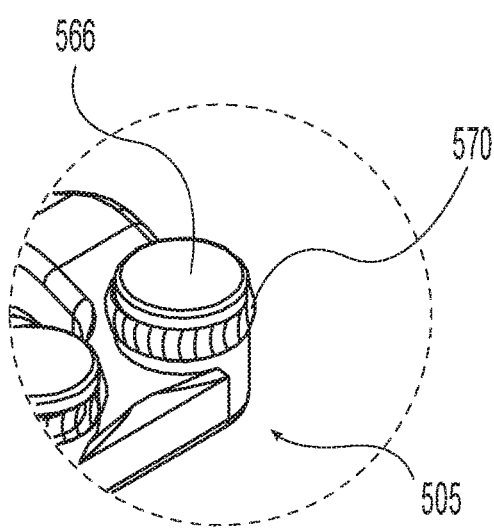
FIG. 25 is a detail perspective view of a portion of the guide of FIG. 24.
Figure 26:
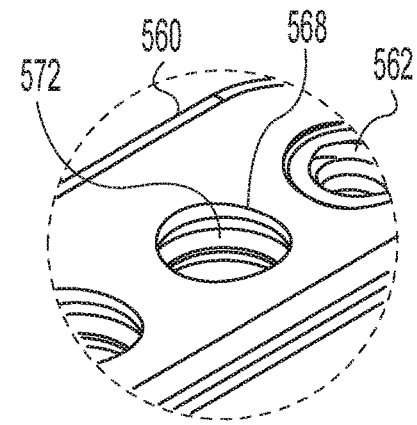
FIG. 26 is a detail perspective view of a portion of the retainer of FIG. 24.

In FIG. 19, the drill and guide tube reducers 230, 292 have been removed. The countersink 330 is driven into the hole 406 to form a countersunk hole into the bone surface. The countersink 330 may be guided by engagement of the cylindrical guide point 332 with the hole 406. Alternatively, or in addition, the countersink 330 may be guided by the guide tubes 213, 290. For example, the diameter 346 of the countersink shaft 346 may be sized to be a slip fit within the guide tubes 213, 290, as shown in the example of FIG. 19. Once the countersink has been driven to a desired depth, the scale 348 on the shank of the countersink may be read relative to the proximal edge 295 of the cap guide tube. The cap guide tube 290 is rigidly linked to the retainer supporting portion 205 and the scale is arranged to indicate the length of screw that when seated in the countersunk hole will engage with the retainer 150 a preferred distance.

Figure 20:
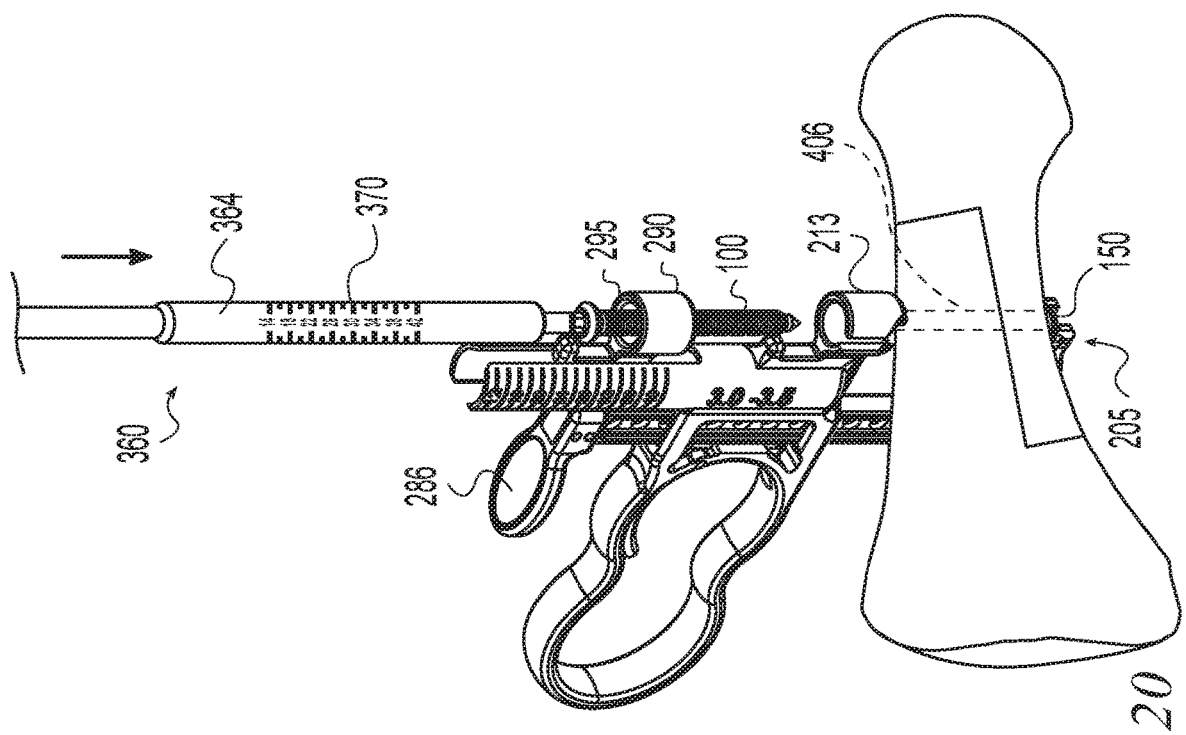

In FIG. 20, the fastener 100 is engaged with the driver 360 and the distal end of the fastener is passed through the guide tubes 213, 290, through the hole 406, and into engagement with the retainer 150. The fastener and retainer are tightened to fix the bone portions together. The fastener 100 may be guided by the hole 406. Alternatively, or in addition, the fastener 100 may be guided by engagement of the driver 360 with the guide tubes 213, 290; e.g. the driver shank 364 may be sized to be a slip fit within the guide tubes as shown in the example of FIG. 20. The scale 370 may be read relative to the proximal edge 295 of the cap guide tube to indicate when the screw is seated in the countersunk hole. If after evaluating the compression of the bone portions, the surgeon determines that more compression is desired, the screw may be driven further to achieve the desired compression. The scale 370 may then be read again to determine a second size screw shorter than the initial screw and the initial screw may be removed and replaced with the second screw if it is desired to limit screw protrusion from the retainer 150.

In FIG. 21, the driver 360 and the guide 200 have been removed. The guide 200 is removed by pressing the handle 202 and cap finger grip 286 together to disengage the pawl 246 and compress the main spring 222. The guide 200 is then moved laterally to disengage the retainer supporting portion 205 from the retainer 150. The fastener 100 is shown with its head 112 seated in the countersunk hole 408 formed by the countersink tool 330 and engaged with the retainer 150 with the distal end 106 extending beyond the retainer.

In FIG. 22, the protruding distal end 106 has been trimmed off such as, for example, with a rod cutter. The illustrative bone repair construct 420 of FIG. 22 includes a scarf osteotomy 422 dividing a metatarsal bone into first and second bone portions 400, 402. The fastener 100 and retainer 150 compress the bone portions together to secure the osteotomy.

In FIG. 23, the instruments and implants of FIGS. 1-14 have been used to fix the bone portions 400, 402 using multiple fasteners. The fasteners may be placed independently of one another with varying lengths and trajectories and with any arbitrary desirable entrance and exit for the holes 412, 414. The illustrative bone repair construct is similar to that of FIG. 21 but with the additional fastener it provides enhanced rotational stability.

Figure 27:
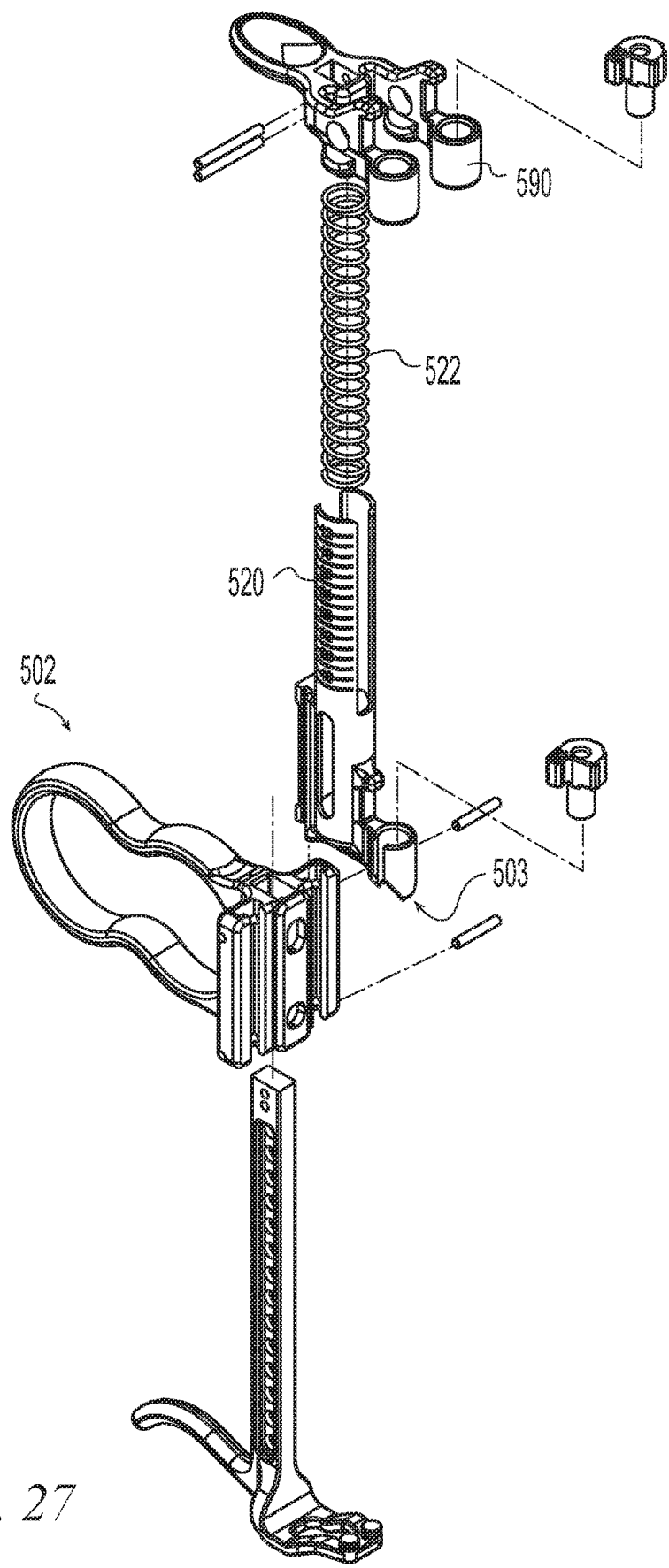
FIG. 27 is a partial exploded perspective view of the guide of FIG. 24, duplicate parts have been omitted for ease of visualization.

FIGS. 24-27 illustrate an alternative guide 500, similar to the guide of FIGS. 7-11, according to one example of the invention. The primary difference between the guide 500 of FIGS. 24-27 and the guide 200 of FIGS. 7-11 is that the guide 500 of FIGS. 24-27 includes a plurality of spring tubes 514 supporting a plurality of distal guide tubes 513 and the retainer supporting member 506 includes a corresponding plurality of proximal guide tubes 590 aligned with the distal guide tubes such that the guide 500 can be used to place multiple fasteners with a single clamping step. Another difference between the guides 200, 500 is that the spring tubes 514 of the guide 500 of FIGS. 24-27 are not fixed to the handle 502 but are mounted for axial translation relative to the handle 502. This allows the bone contacting portions 503 to be axially offset with respect to one another so that the main springs 522 can independently bias the bone contacting portions into contact with different screw placement areas of a bone portion having non-uniform thickness. The indicia 520 on the spring tubes 514 will independently indicate the screw length needed for each screw placement area on the bone portion. The guide 500 may be configured to support multiple retainers similar to retainer 150. Alternatively, the guide 500 may be configured as shown to support a retainer 560, such as a plate, with multiple receivers 562. In the illustrative example of FIGS. 24-27, the retainer supporting portion 505 includes projections 566 engageable with holes 568 in the retainer 560 to releasably secure the retainer 560 to the retainer supporting portion 505. A circumferential spring 570 mounted on each projection 566 presses into a groove 572 in each hole 568 to secure the retainer 560 in snap fit relationship. Preferably the receivers 562 are positioned outboard relative to the holes 568 in the retainer to maximize the fastener span on the retainer 560. The guide tube axes 524 are oriented to intersect the retainer coaxial with the receiver axes 554. In FIG. 27, duplicate parts have been omitted for ease of visualization. In the illustrative example of FIGS. 24-27, the guide 500 provides for placing two fasteners with predetermined relative spacing and trajectories.

Figure 28:
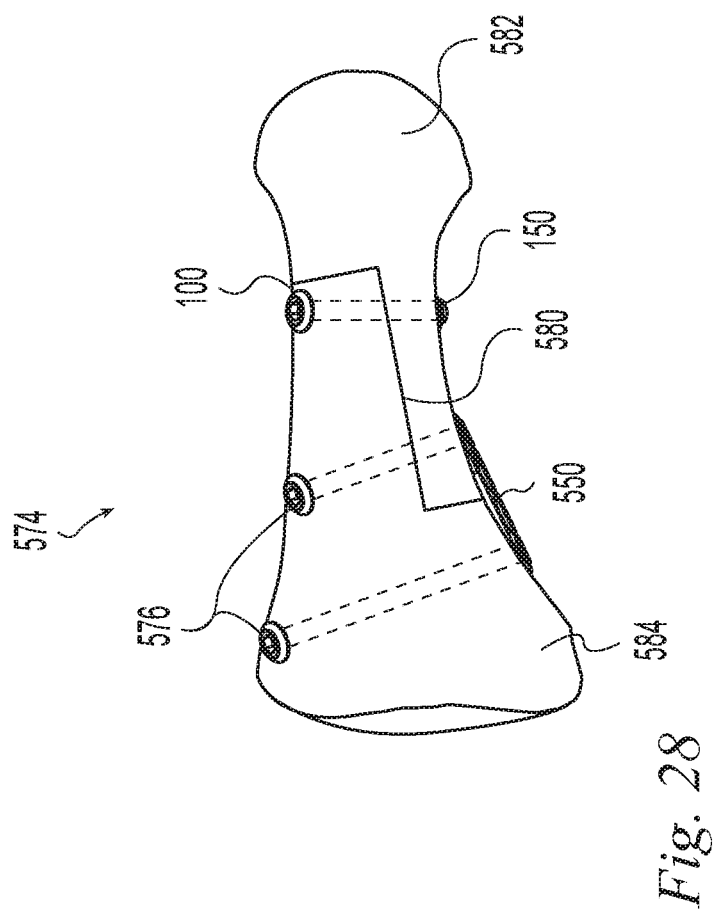
FIG. 28 illustrates a bone repair according to one example of the invention using the implants and instruments of FIGS. 1-14 and FIGS. 24-27.
Figure 29:
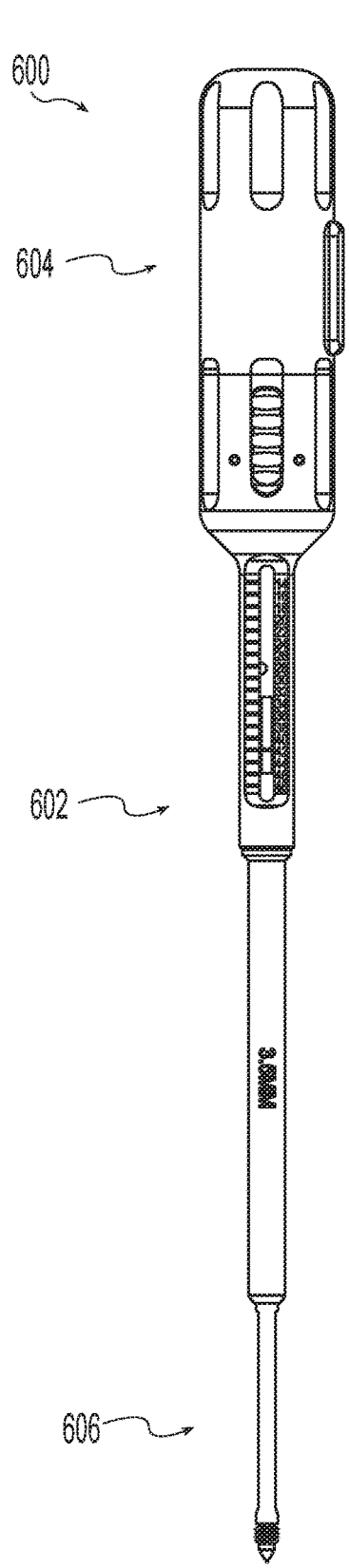
FIG. 29 is a front view of a compressor instrument according to one example of the invention.
Figure 30:
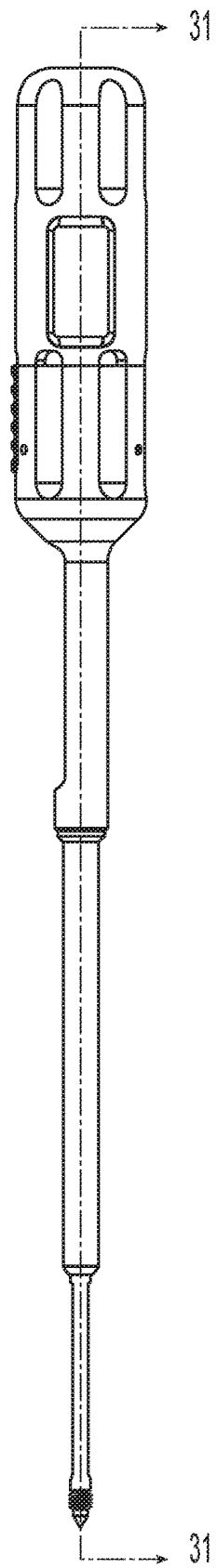
FIG. 30 is a side view of a compressor instrument of FIG. 29.
Figure 31:
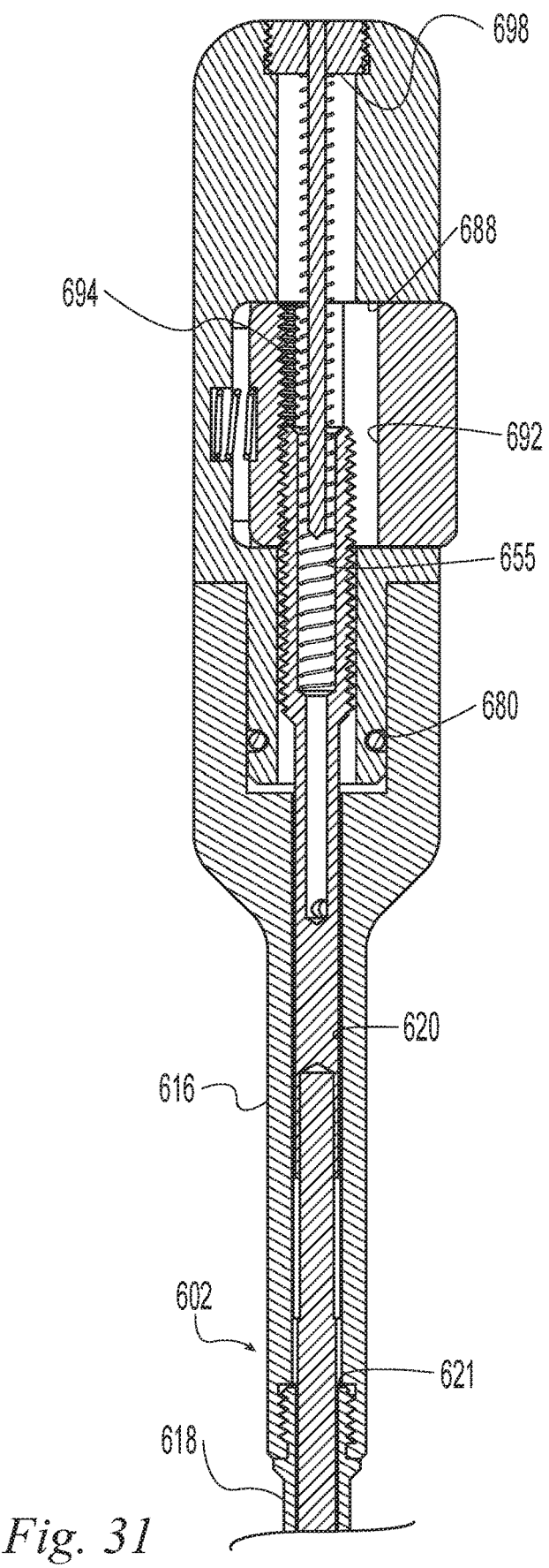
FIG. 31 is a cross-sectional view of the proximal portion of the compressor instrument of FIG. 29 taken along line 31-31 of FIG. 30.
Figure 32:
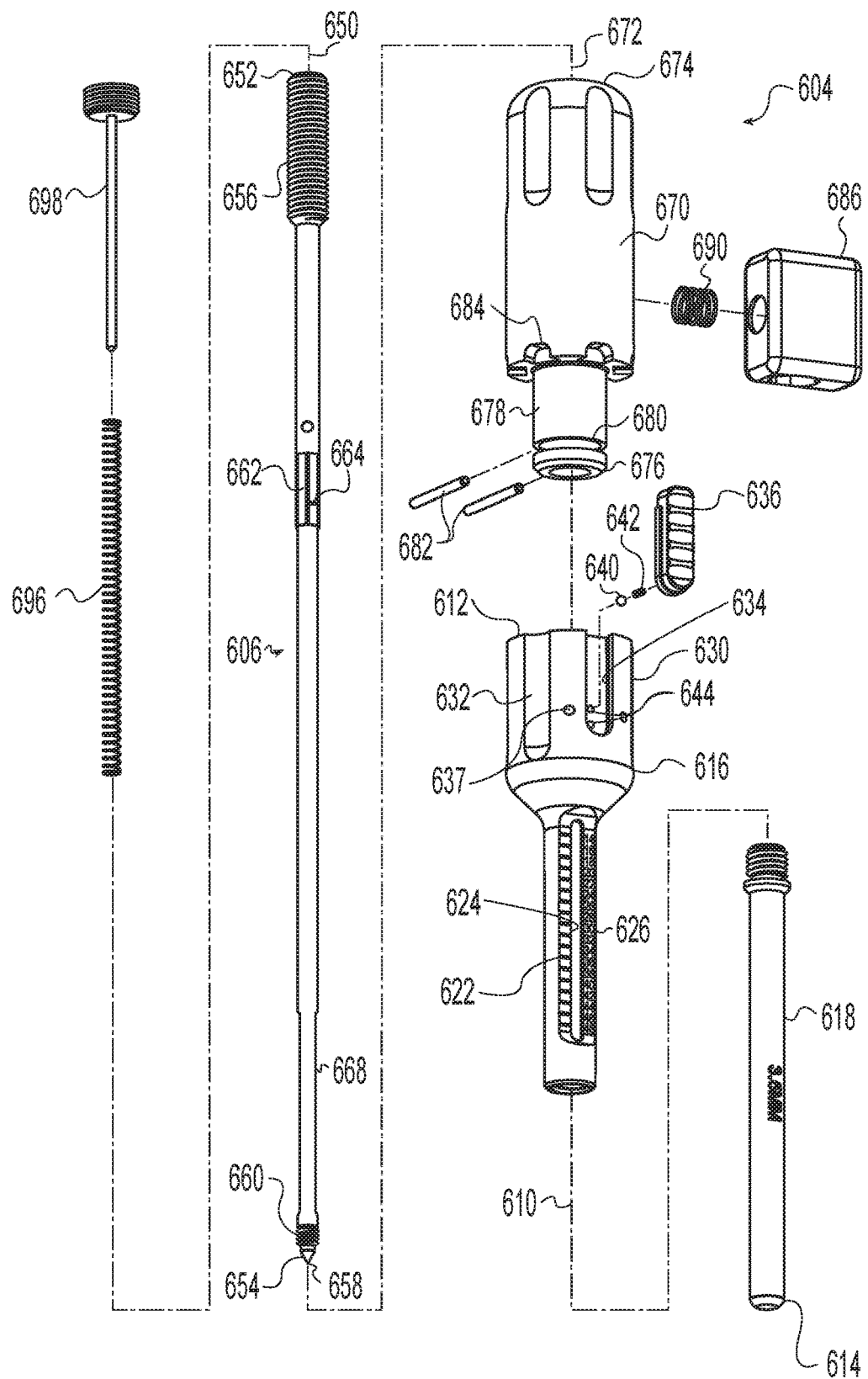
FIG. 32 is n exploded perspective view of the compressor instrument of FIG. 29.

FIG. 28 illustrates a bone repair construct 574 created using the implants and instruments of FIGS. 1-14 and FIGS. 24-27. First and second fasteners 576 and a retainer 550 are placed using the guide 500 of FIGS. 24-27 according to one example of the invention. A third fastener 100 and a retainer 150 are independently placed using the guide 200 of FIGS. 7-11. The illustrative bone repair construct 574 of FIG. 28 includes a scarf osteotomy 580 dividing a metatarsal bone into first and second bone portions 582, 584. The plate like retainer 550 coupled with two fasteners 576 spans the proximal portion of the osteotomy cut on the plantar side of the osteotomy to secure the osteotomy where it is in tension. The third fastener 100 and retainer 150 secures the distal portion of the osteotomy and provides rotational stability to the osteotomy.

FIGS. 29-32 illustrate a compressor instrument 600 according to one example of the invention useable with the implants, instruments, and methods of the examples of FIGS. 1-28. The compressor 600 includes a body 602, a handle 604, and a shaft 606. The shaft 606 is axially translatable within the body by manipulating the handle. The details of these components will be explained in reference to the drawings and in particular with reference to FIGS. 31 and 32.

The body 602 is an elongate hollow structure defining a longitudinal axis 610 extending between a proximal end 612 and a distal end 614. The body may be made as a single piece or as an assembly of pieces. In the example of FIGS. 29-32 the body 602 is a two-part assembly including a proximal body portion 616 distal body portion 618 joined together. The portions may be joined by any suitable method including welding, pinning, threading, and/or other joining method. In the example of FIGS. 29-32, the proximal body portion 616 and distal body portion 618 are threaded together and then welded. The body 602 includes an axial passage 620 for receiving the shaft 606. At least a portion of the passage 620 has a hexagonally shaped cross-section. Preferably the proximal portion of the passage is hexagonal and a shoulder 621 is formed in the passage 620. In the example of FIGS. 29-32, the proximal body portion includes a hexagonal passage and the distal body portion includes a cylindrical passage. The cylindrical passage has a diameter less than the distance across corners of the hexagonal passage such that a shoulder 621 is formed where the two passages join. The distal portion 618 of the body is a narrow tube and the distal end 614 approximates the size and shape of the tapered bottom surface 116 of the head of the fastener 100 of FIGS. 1-3. A mid portion 622 of the body, formed on the distal end of the proximal body portion 616, includes an elongated slot 624 communicating with the passage 620. A scale 626 is positioned adjacent the slot 624. The proximal end of the proximal body portion 616 flares outwardly to form an enlarged receiver 630. The outer surface of the receiver 630 includes elongate grooves 632 spaced axially about the receiver. The grooves are closed distally and open at the proximal end 612. One of the grooves 634 is undercut to receive a handle lock 636 in axial sliding relationship. A ball 640 and spring 642 are captured in a recess (not shown) in the handle lock 636 and cooperate with a pair of detents 644 to create 2 distinct positions for the handle lock. The handle lock may be moved distally into a handle unlocked position and proximally into a handle locked position. The receiver includes pin holes 637.

The shaft 606 defines a longitudinal axis 650 extending between a proximal end 652 and a distal end 654. Drive threads 656 are formed adjacent the proximal end 652. The distal end of the shaft is sized and shaped to correspond with the distal end of fastener 100 of FIGS. 1-3 including a tapered point 658 and screw threads 660. The mid portion of the shaft 606 includes a hexagonally shaped portion 662 sized to slide within the hexagon portion of the passage 620 to allow the shaft to translate axially while preventing the shaft from rotating relative to the body 602. The hexagonal portion 662 abuts the shoulder 621 to limit distal motion of the shaft. An indicator 664 on the shaft is visible through the slot 624 in the body so that the indicator position may be read relative to the scale 626. In the example of FIGS. 29-32, the indicator is a line etched across a flat of the hexagonally shaped portion 662. A relieved portion 668 of the shaft has a reduced diameter beginning just proximal to the distal threads 660 to prevent the shaft from binding when it is inserted into a passage in a bone. A spring bore 665 is formed into the shaft from the proximal end.

The handle 604 includes an elongated stepped cylindrical body 670 defining a longitudinal axis 672 extending between a proximal end 674 and a distal end 676. A distal portion 678 of the handle has a reduced diameter sized to fit coaxially within the receiver 630 of the body 602 in rotating relationship. A circumferential groove 680 is formed in the distal portion 678 of the handle and aligns with the pin holes 637 in the body such that with the distal portion 678 of the handle inserted into the receiver 630, pins 682 may be inserted into the pin holes 637 and tangentially within the groove 680 to secure the handle 604 in the body 602 axially while permitting the handle to rotate relative to the body. The handle includes notches 684 that may be aligned with the elongate grooves 632 of the body. The handle lock 636 may be moved proximally so that it engages one of the notches 684 to lock the handle and body together for rotation. The handle lock 636 may be moved distally so that it is disengaged from the notches 684 to permit the handle to rotate relative to the body. A quick release 686 is mounted in a cavity 688 in the side of the handle for translation into and out of the cavity 688. A quick release spring 690 biases the quick release outwardly. A passage 692 axially through the quick release includes half-threads 694 formed on one side of the passage 692. The shaft is assembled to the other components by inserting the distal end of the shaft 606 into the proximal end 674 of the handle 604, through the quick release 686, through the body and out the distal end 614. A shaft spring 698 is inserted into the spring bore 655 of the shaft. A spring retainer 698 is inserted into the shaft spring and coupled to the handle 604. In the example of FIGS. 29-32, the spring retainer 698 has an enlarged threaded head that threads into a corresponding thread in the proximal end of the handle 604. The shaft spring 698 biases the shaft distally. The quick release spring biases the half-thread 694 of the quick release into engagement with the drive thread 656 formed on the proximal end of the shaft.

In use, pressing the quick release inwardly, disengages the half-thread 694 from the drive thread 656. With the half-thread 694 disengaged, the shaft is free to translate distally relative to the body 602 under the influence of the shaft spring 696. Likewise, with the half-thread 694 disengaged, the shaft may be pressed proximally back into the body 602 against the shaft spring 696. Releasing pressure from the quick release allows the quick release spring 690 to bias the half-threads into engagement with the drive threads. With the half-threads engaged, the shaft is no longer freely translatable but must be translated by rotating the handle 604 relative to the body 602 to threadingly advance or retract the shaft 606.

Figure 33:
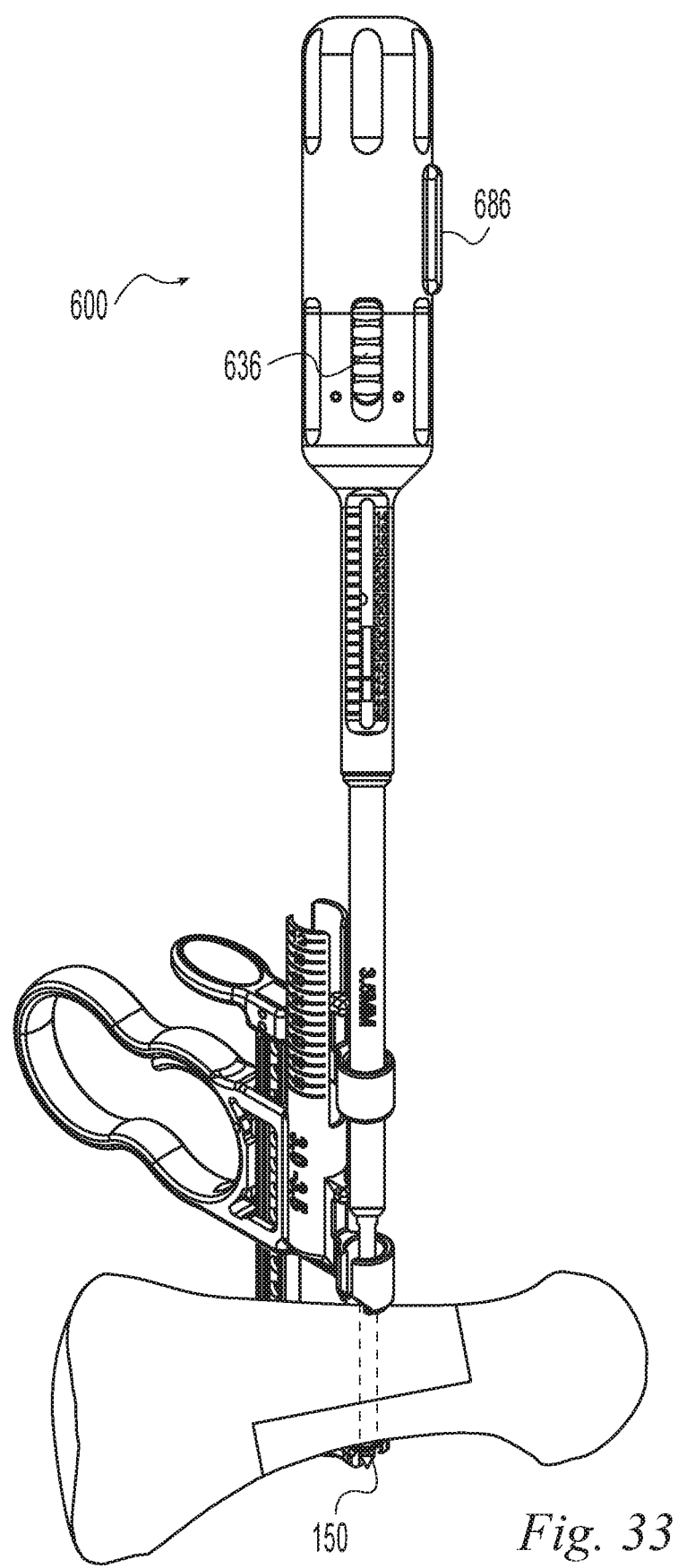
FIGS. 33 and 34 are perspective views illustrating a method of using the compressor instrument according to one example of the invention.
Figure 34:
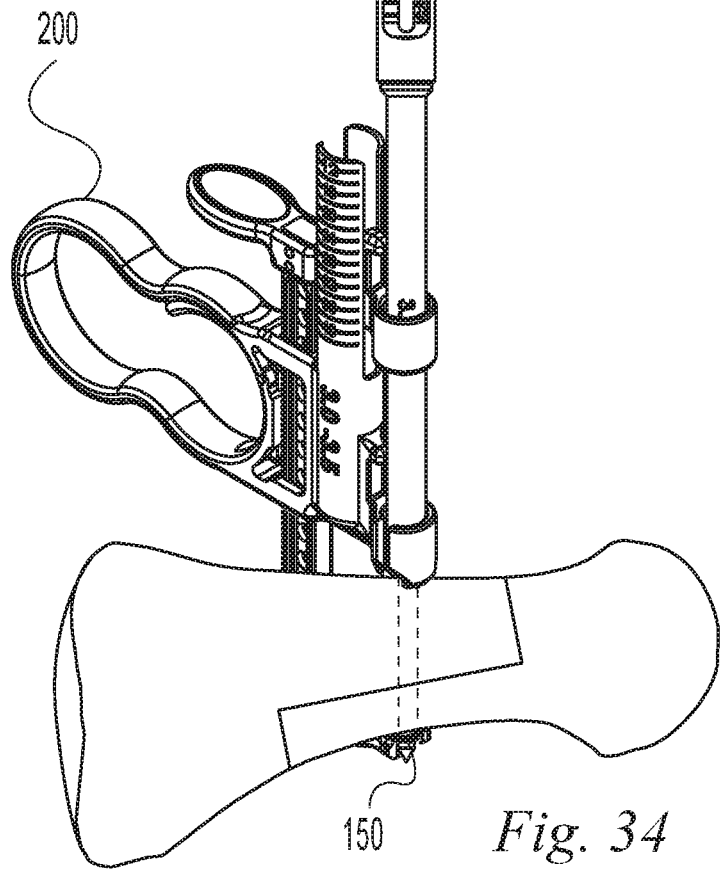
Figure 35:
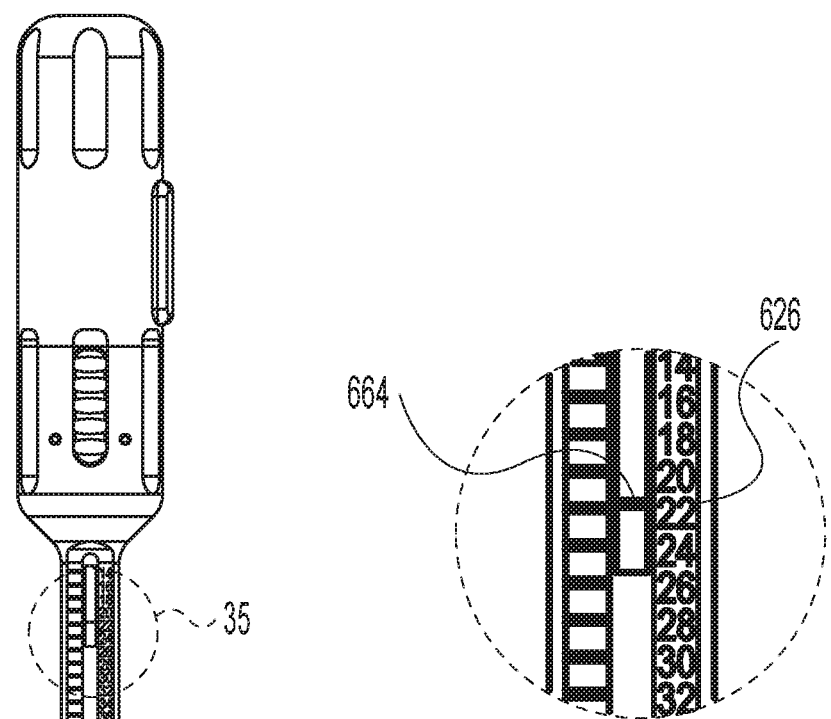
FIG. 35 is a detail view of a portion of the compressor instrument.

FIGS. 33-35 illustrate the use of the compressor 600 in a surgical procedure. In one example, the compressor may be used in the method illustrated in FIGS. 15-23 before inserting the screw as shown in FIG. 20. The handle lock 636 is moved to its proximal position to lock the handle and body rotationally. The quick release 686 is depressed to release the half-thread and allow the shaft to extend distally. The quick release may then be released. As shown in FIG. 33 the shaft is inserted through the bone to engage the threaded distal end of the shaft with the retainer 150. The handle, body, and shaft are rotated together to thread the shaft into the retainer as far as it will go. The quick release 686 is then depressed to disengage the half-thread and the handle and body are pressed downwardly over the shaft until the distal end 614 of the body contacts the bone as shown in FIG. 34. The handle lock 636 is moved to its distal position to free the handle. The handle is rotated relative to the body such that the half-thread 694 drives the drive thread 656 to retract the shaft into the body and compress the bone between the distal end 614 of the body and the retainer 150. The handle is rotated until a desired level of compression is achieved. In the example of FIGS. 29-35, the indicator 626 will indicate on the scale 626 the length of screw necessary to achieve the current level of compression. If the indicated length corresponds to an available screw length, then that screw size is selected. If the indicated length falls between two available screw lengths, then the longer length is selected to insure sufficient engagement of the screw with the retainer. In the example of FIGS. 29-35, screws are provided in 2 mm increments and this method will result in a construct with the tip of the screw recessed slightly in the retainer, 0.5 mm at a minimum, or with the screw tip extending slightly from the retainer, 1.5 mm at a maximum. While the compressor is still in position, the guide 200 may be tightened again as shown in FIG. 17 to retain the compression achieved by the compressor. The compressor is then removed and the appropriate length screw implanted. By using the compressor, the bone is fully compressed to a desired level prior to inserting the screw such that accurately sized blunt tipped screws may be used and the step of cutting off the tip of the screw as shown in FIG. 22 may be omitted.

Various examples have been illustrated and described including the following list of examples. The examples are illustrative but not limiting of the scope of the invention. The various examples may be substituted and combined and other alterations made within the scope of the invention. For example, among other substitutions, male and female features may be reversed.

1. A system operable to fix first and second bone portions relative to one another, the system comprising:
   a. a retainer having a receiver defining a receiver longitudinal axis;
   b. a screw threadably engageable with the receiver, the screw having a shaft portion defining a longitudinal axis, the shaft having a distal shaft width dimension perpendicular to the screw longitudinal axis in a width direction, a proximal shaft width dimension having a width dimension perpendicular to the screw longitudinal axis in the width direction greater than the distal shaft width dimension; and
   c. a guide having a handle, a bone contacting member mounted to the handle, a retainer supporting member mounted to the handle opposite the bone contacting member, the retainer supporting member having a portion operable to releasably support the retainer opposite the bone contacting member, the bone contacting member and retainer supporting member being mounted for translation relative to one another and being resiliently biased toward one another, the guide being operable to clamp an object between the retainer and bone contacting member while the screw is engaged with the retainer.

2. The system of example number 1 wherein the guide comprises a first guide tube defining an insertion axis and operable to guide a drill having a diameter less than the proximal shaft width dimension and operative to permit passage of the screw along the insertion axis.

3. The system of example number 2 comprising a removable guide tube reducer having a central bore, the guide tube reducer being removably received in the first guide tube coaxial with the insertion axis, the central bore operable to receive a drill to guide the drill along the insertion axis.

4. The system of example number 2 wherein the first guide tube is rigidly mounted to the retainer supporting member and the bone contacting member includes a second guide tube, the first and second guide tubes being spaced apart longitudinally and coaxially aligned.

5. The system of example number 1 wherein at least one of the bone contacting member and the retainer supporting member engage the handle in a rack and pawl arrangement in which a pawl is moveable between a first position in which a rack is moveable longitudinally relative to the pawl in a first rack direction but is prevented from moving longitudinally relative to the pawl in a second rack direction opposite the first rack direction due to engagement of the pawl with the rack, and a second position in which the rack is moveable in the second rack direction, the retainer supporting member being resiliently biased in the first rack direction.

6. The system of example number 5 wherein the retainer supporting member comprises a first grip and a second grip such that pressing the first grip and the handle toward one another moves the bone contacting member and the retainer supporting member away from one another and pressing the second grip and the handle toward one another moves the bone contacting member and retainer supporting member toward one another.

7. The system of example number 6 wherein the guide is responsive to pressing the first grip and the handle toward one another to move the pawl into the second position and move the bone contacting member and retainer supporting member away from one another to permit an object to be placed between the bone contacting member and retainer supporting member, the guide being responsive to releasing compression between the first grip and the handle to bias the bone contacting member and retainer supporting member toward one another under spring pressure to grip the object with a first compressive force and bias the pawl into the first position, the guide being responsive to pressing the second grip and the handle toward one another to grip the object with a second compressive force greater than the first compressive force and maintain the second compressive force by engagement of the rack and pawl.

8. The system of example number 1 wherein the retainer supporting member comprises a retainer seat operable to receive the retainer in a direction transverse to the receiver longitudinal axis.

9. The system of example number 8 wherein the retainer and retainer seat engage in a tongue and groove arrangement that resists translation of the retainer relative to the retainer seat along the receiver longitudinal axis.

10. The system of example number 9 wherein the retainer seat comprises a pair of resilient arms that grip the retainer.

11. The system of example number 10 wherein the arms surround a portion of the periphery of the retainer, the arms being operable to receive and release the retainer in a snap-fit relationship.

12. The system of example number 8 further comprising a retainer handle removably engageable with the retainer, the retainer handle being engageable with and releasable from the retainer receiver along the receiver longitudinal axis.

13. The system of example number 10 further comprising a retainer handle releasably engaged with the retainer and operable to apply a transverse force to the retainer as it is engaged with the arms, the retainer handle being removable from the retainer after the retainer is engaged with the arms.

14. The system of example number 13 wherein the retainer handle is threadably engageable with the retainer in a first direction parallel to the motion axis and the screw is threadably engageable with the retainer in a second direction opposite the first direction.

15. The system of example number 27 wherein the retainer handle and screw are threadably engageable with a single threaded bore through the retainer.

16. A system for fixing first and second bone portions relative to one another, the system comprising:
   a. a retainer;
   b. a fastener engageable with the retainer;
   c. a guide comprising:
      i. a handle;
      ii. a bone contacting member mounted to the handle;
      iii. a retainer supporting member mounted to the handle opposite the bone contacting member, the retainer supporting member having a portion operable to releasably support the retainer opposite the bone contacting member, the bone contacting member and retainer supporting member being mounted for translation relative to one another, the retainer supporting member having a first grip and a second grip such that pressing the first grip and the handle toward one another moves the bone contacting member and retainer supporting member away from one another and pressing the second grip and the handle toward one another moves the bone contacting member and retainer supporting member toward one another.

17. The system of example number 16 wherein the retainer supporting member engages the handle in a rack and pawl arrangement in which a pawl is moveable between a first position in which a rack is moveable longitudinally relative to the pawl in a first rack direction but is prevented from moving longitudinally relative to the pawl in a second rack direction opposite the first rack direction due to engagement of the pawl with the rack, and a second position in which the rack is moveable in the second rack direction, the retainer supporting member being resiliently biased in the first rack direction, the pawl being resiliently biased into the first position and the pawl including an extension positioned adjacent the handle such that applying pressure to press the first grip and the handle toward one another moves the pawl into the second position allowing the rack to move in the second rack direction and releasing pressure allows the pawl to be biased to the pawl first position.

18. The system of example number 17 wherein the guide is responsive to pressing the first grip and the handle toward one another to move the pawl into the second position and move the bone contacting member and retainer supporting member away from one another to receive a bone portion between the bone contacting member and retainer supporting member, the guide being responsive to releasing compression between the first grip and the handle to bias the bone contacting member and retainer supporting member toward one another under spring pressure to grip the bone portion with a first compressive force and bias the pawl into the first position, the guide being responsive to pressing the second grip and the handle toward one another to grip the bone portion with a second compressive force greater than the first compressive force and maintain the second compressive force by engagement of the rack and pawl.

19. A system for fixing first and second bone portions relative to one another, the system comprising:
    a. a retainer;
    b. a screw threadably engageable with the retainer;
    c. a guide having a bone contacting portion, an opposed retainer supporting portion operable to releasably retain the retainer opposite the bone contacting portion, the bone contacting portion and retainer supporting portion defining a motion axis and being mounted for axial translation parallel to the motion axis toward and away from one another; the retainer supporting portion comprising spaced apart arms defining a perimeter greater than one half a perimeter of the retainer and being operable to spread apart to receive the retainer as the retainer is pressed between the arms and spring back to positively grip the retainer.

20. The system of example number 21 wherein the retainer and arms engage in torque transmitting relationship operable to resist rotation of the retainer as the screw is threadably engaged with the retainer.

21. The system of example number 20 wherein the torque transmitting relationship is defined by features formed on the retainer and the arms that engage when the retainer is received by the arms by pressing the retainer in a direction transverse to the motion axis, the features being operable to self-align as the retainer engages the arms.

22. The system of example number 21 further comprising a retainer handle releasably engaged with the retainer and operable to apply a transverse force to the retainer as it is engaged with the arms, the retainer handle being removable from the retainer after the retainer is engaged with the arms.

23. A method of fixing first and second bone portions together, the method comprising:
    a. separating opposing jaws of a clamp counter to a resilient biasing member;
    b. positioning the jaws adjacent the first and second bone portions;
    c. allowing the resilient biasing member to bias the jaws into clamping engagement with the first and second bone portions, the resilient biasing member creating a first clamping pressure between the jaws and the first and second bone portions;
    d. pressing the jaws together to create a second clamping pressure between the jaws and the first and second bone portions, the second clamping pressure being greater than the first clamping pressure;
    e. preventing the jaws from moving apart.

24. The method of example number 23 wherein preventing the jaws from moving apart comprises engaging a pawl with a rack 25. The method of example number 23 wherein separating opposing jaws comprises pressing a first handle and a second handle toward one another, wherein pressing one of the handles disengages a pawl from a rack to permit the handles to move toward one another.

26. The method of example number 23 further comprising:
    a. using the clamp to guide a drill to form a hole in at least one of the first and second bone portions;
    b. using the clamp to support a retainer adjacent the bone; and
    c. passing a fastener through the hole and into engagement with the retainer while the clamp is engaged with the bone portions.

27. The method of example number 26 further comprising trimming a portion of the fastener that extends through the retainer.

28. The method of example number 26 further comprising using the clamp to guide a countersink to countersink the hole.

29. A method of fixing first and second bone portions together, the method comprising:
    a. clamping the first and second bone portions together with a clamp, the clamp supporting a retainer against a surface of the bone;
    b. inserting a fastener through at least one of the first and second bone portions;
    c. engaging the fastener with the retainer in axial force transmitting relationship;
    d. trimming a portion of the fastener that extends beyond the retainer; and
    e. removing the clamp.

30. The method of example number 29 wherein trimming a portion of the fastener is done after the clamp is removed.

31. A method of fixing first and second bone portions together, the method comprising:
    a. clamping the first and second bone portions between first and second jaws of a bone clamp, the clamp supporting a retainer against a first surface of at least one of the first and second bone portions;
    b. inserting a compressor through the first and second bone portions;
    c. engaging a first portion of the compressor with the retainer and a second portion of the compressor with a second surface of at least one of the first and second bone portions; and
    d. actuating the compressor to move the first portion of the compressor toward the second portion of the compressor and compress the first and second bone portions between the retainer and the second portion of the compressor.

32. The method of example number 31 further comprising, after actuating the compressor, reading indicia associated with the compressor to determine a fastener length.

33. The method of example number 32 further comprising tightening the clamp to maintain the compression created by the compressor.

34. The method of example number 33 further comprising, after tightening the clamp, disengaging the compressor from the retainer.

35. The method of example number 34 further comprising, after disengaging the compressor, selecting a fastener corresponding to the determined fastener length, inserting the fastener through the first and second bone portions, engaging the fastener with the retainer, tightening the fastener to fix the first and second bone portions together.

36. The method of example number 35 further comprising, before engaging the first portion of the compressor with the retainer, extending the first portion of the compressor away from the second portion of the compressor.

37. The method of example number 36 wherein extending the first portion of the compressor away from the second portion of the compressor comprises actuating a quick release mechanism allowing the first and second portion of the compressor to move apart under a resilient biasing force.

38. The method of example number 37 wherein actuating the compressor to move the first portion of the compressor toward the second portion of the compressor comprises rotating a first threaded portion of the compressor relative to a second threaded portion of the compressor.

39. The method of example number 38 further comprising releasing an anti-rotation lock prior to rotating the first threaded portion of the compressor relative to a second threaded portion of the compressor.

40. A method of fixing first and second bone portions together, the method comprising:
 a. clamping the first and second bone portions together with a clamp, the clamp supporting a retainer against a surface of the bone, the clamp having a first guide member aligned with a first receiver associated with the retainer, the clamp having a second guide member aligned with a second receiver associated with the retainer;
 b. guiding a hole forming instrument with the first guide member to form a first hole through at least one of the first and second bone portions and aligned with the first receiver;
 c. guiding a hole forming instrument with the second guide member to form a second hole through at least one of the first and second bone portions and aligned with the second receiver;
 d. inserting a first fastener through the first hole and into engagement with the first receiver in axial force transmitting relationship;
 e. inserting a second fastener through the second hole and into engagement with the second receiver in axial force transmitting relationship; and
 f. removing the clamp.

41. The method of example number 40 wherein the clamp has a first bone contacting portion and a second bone contacting portion, the first and second bone contacting portions being independently translatable relative to the bone, each of the first and second bone contacting portions being independently resiliently biased into contact with the bone.

42. The method of example number 41 wherein each of the bone contacting portions has linked to it indicia indicating a recommended fastener length, the method further comprising reading the indicia associated with each bone contacting portion and selecting corresponding first and second fasteners.

What is claimed is:

1. A system operable to fix first and second bone portions relative to one another, the system comprising:
 a retainer having a receiver defining a receiver longitudinal axis;
 a screw threadably engageable with the receiver, the screw having a shaft portion defining a longitudinal axis, the shaft portion having a distal shaft width dimension perpendicular to the screw longitudinal axis in a width direction, a proximal shaft width dimension perpendicular to the screw longitudinal axis in the width direction, the proximal shaft width dimension being greater than the distal shaft width dimension; and
 a guide having a handle, a bone contacting member mounted to the handle, and a retainer supporting member mounted to the handle opposite the bone contacting member, the retainer supporting member having a portion configured to releasably support the retainer opposite the bone contacting member, the bone contacting member and the retainer supporting member being mounted for translation relative to one another and being resiliently biased toward one another, wherein the guide is configured to clamp the first and second bone portions, together, between the retainer and the bone contacting member while the screw is engaged with the retainer;
 wherein the guide comprises a first guide tube defining an insertion axis and is operable to guide a drill having a diameter less than the proximal shaft width dimension of the shaft portion of the screw and is operative to permit passage of the screw along the insertion axis.

2. The system of claim 1 further comprising a removable guide tube reducer having a central bore, the guide tube reducer being removably received in the first guide tube coaxial with the insertion axis, the central bore operable to receive a drill to guide the drill along the insertion axis.

3. The system of claim 1 wherein at least one of the bone contacting member and the retainer supporting member engage the handle in a rack and pawl arrangement wherein a pawl is moveable between a first position in which a rack is moveable longitudinally relative to the pawl in a first rack direction but is prevented from moving longitudinally relative to the pawl in a second rack direction opposite the first rack direction due to engagement of the pawl with the rack, and a second position in which the rack is moveable in the second rack direction, the retainer supporting member being resiliently biased in the first rack direction.

4. The system of claim 3 wherein the retainer supporting member comprises a first grip and a second grip and wherein pressing the first grip and the handle toward one another moves the bone contacting member and the retainer supporting member away from one another and pressing the second grip and the handle toward one another moves the bone contacting member and retainer supporting member toward one another.

5. The system of claim 4 wherein the guide is configured such that pressing the first grip and the handle toward one another moves the pawl into the second position and moves the bone contacting member and the retainer supporting member away from one another to permit the first and second bone portions to be placed between the bone contacting member and the retainer supporting member, wherein releasing compression between the first grip and the handle biases the bone contacting member and the retainer supporting member toward one another under spring pressure to grip the first and second bone portions with a first compressive force and biases the pawl into the first position, and wherein pressing the second grip and the handle toward one another grips the first and second bone portions with a second compressive force greater than the first compressive force and maintains the second compressive force by engagement of the rack and the pawl.

6. The system of claim 1 wherein the retainer supporting member comprises a retainer seat operable to receive the retainer in a direction transverse to the receiver longitudinal axis.

7. The system of claim 6 further comprising a retainer handle removably engageable with the retainer, the retainer handle being engageable with and releasable from the retainer receiver along the receiver longitudinal axis.

8. The system of claim 6 wherein the retainer and the retainer seat engage in a tongue and groove arrangement that resists translation of the retainer relative to the retainer seat along the receiver longitudinal axis.

9. The system of claim 8 wherein the retainer seat comprises a pair of resilient arms that grip the retainer.

10. The system of claim 9 wherein the arms surround a portion of the periphery of the retainer, the arms being operable to receive and release the retainer in a snap-fit relationship.

11. The system of claim 9 further comprising a retainer handle releasably engaged with the retainer and operable to apply a transverse force to the retainer as it is engaged with the arms, the retainer handle being removable from the retainer after the retainer is engaged with the arms.

12. The system of claim 11 wherein the retainer handle is threadably engageable with the retainer in a first direction parallel to a motion axis and the screw is threadably engageable with the retainer in a second direction opposite the first direction.

13. The system of claim 11 wherein the retainer handle and the screw are threadably engageable with a single threaded bore through the retainer.

14. A system for fixing first and second bone portions relative to one another, the system comprising:
a retainer;
a fastener engageable with the retainer;
a guide comprising:
  a handle;
  a bone contacting member mounted to the handle;
  a retainer supporting member mounted to the handle opposite the bone contacting member, the retainer supporting member having a portion operable to releasably support the retainer opposite the bone contacting member, the bone contacting member and the retainer supporting member being mounted for translation relative to one another, the retainer supporting member having a first grip and a second grip wherein actuating the first grip and the handle toward one another moves the bone contacting member and the retainer supporting member away from one another and actuating the second grip and the handle toward one another moves the bone contacting member and the retainer supporting member toward one another;
wherein the retainer supporting member engages the handle in a rack and pawl arrangement wherein a pawl is moveable between a first position in which a rack is moveable longitudinally relative to the pawl in a first rack direction but is prevented from moving longitudinally relative to the pawl in a second rack direction opposite the first rack direction due to engagement of the pawl with the rack, and a second position in which the rack is moveable in the second rack direction, the retainer supporting member being resiliently biased in the first rack direction, the pawl being resiliently biased into the first position and the pawl including an extension positioned adjacent the handle such that applying pressure to press the first grip and the handle toward one another moves the pawl into the second position allowing the rack to move in the second rack direction and releasing pressure allows the pawl to be biased to the pawl first position.

15. The system of claim 14 wherein the guide is configured such that pressing the first grip and the handle toward one another moves the pawl into the second position and moves the bone contacting member and the retainer supporting member away from one another to receive a bone portion between the bone contacting member and the retainer supporting member, wherein releasing compression between the first grip and the handle biases the bone contacting member and the retainer supporting member toward one another under spring pressure to grip the bone portion with a first compressive force and biases the pawl into the first position, and wherein pressing the second grip and the handle toward one another grips the bone portion with a second compressive force greater than the first compressive force and maintains the second compressive force by engagement of the rack and pawl.

16. A system for fixing first and second bone portions relative to one another, the system comprising:
a retainer;
a screw threadably engageable with the retainer;
a guide having a bone contacting portion and an opposed retainer supporting portion operable to releasably retain the retainer opposite the bone contacting portion, the bone contacting portion and the retainer supporting portion defining a motion axis and being mounted for axial translation parallel to the motion axis toward and away from one another; the retainer supporting portion comprising spaced apart arms defining a perimeter greater than one half a perimeter of the retainer and being operable to spread apart to receive the retainer as the retainer is pressed between the arms and spring back to positively grip the retainer;
wherein the retainer and the arms engage in a torque transmitting relationship operable to resist rotation of the retainer as the screw is threadably engaged with the retainer, wherein the torque transmitting relationship is defined by features formed on the retainer and the arms that engage when the retainer is received by the arms by pressing the retainer in a direction transverse to the motion axis, the features being operable to self-align as the retainer engages the arms.

17. The system of claim 16 wherein the guide is configured to clamp the first and second bone portions, together, between the retainer and the bone contacting portion while the screw is engaged with the retainer.

18. The system of claim 16 further comprising a retainer handle releasably engaged with the retainer and operable to apply a transverse force to the retainer as it is engaged with the arms, the retainer handle being removable from the retainer after the retainer is engaged with the arms.

* * * * *